United States Patent
Zaima et al.

(10) Patent No.: US 10,042,984 B2
(45) Date of Patent: Aug. 7, 2018

(54) SYSTEM AND METHOD FOR MONITORING HAND HYGIENE

(71) Applicant: Sterilogy, LLC, Bloomfield Hills, MI (US)

(72) Inventors: Harold H. Zaima, Bloomfield Hills, MI (US); Bradley D. Ahlgren, Bloomfield Hills, MI (US)

(73) Assignee: STERILOGY, LLC, Bloomfield Hills, MI (US)

( * ) Notice: Subject to any disclaimer, the term of this patent is extended or adjusted under 35 U.S.C. 154(b) by 294 days.

(21) Appl. No.: 14/695,530

(22) Filed: Apr. 24, 2015

(65) Prior Publication Data

US 2015/0227705 A1    Aug. 13, 2015

Related U.S. Application Data

(63) Continuation-in-part of application No. 14/474,617, filed on Sep. 2, 2014, now Pat. No. 9,027,795, which
(Continued)

(51) Int. Cl.
*B67D 7/06* (2010.01)
*B67D 7/56* (2010.01)
(Continued)

(52) U.S. Cl.
CPC ............ *G06F 19/3406* (2013.01); *A45F 5/00* (2013.01); *A45F 5/02* (2013.01); *A45F 5/021* (2013.01);
(Continued)

(58) Field of Classification Search
CPC ........... G06F 19/3406; A45F 5/00; A45F 5/02
(Continued)

(56) References Cited

U.S. PATENT DOCUMENTS

| D127,009 S | 3/1941 | Gebhart et al. |
|---|---|---|
| 3,363,968 A | 1/1968 | Williams |

(Continued)

FOREIGN PATENT DOCUMENTS

| GB | 2340190 A1 | 2/2000 |
|---|---|---|
| WO | WO 2008 119158 A1 | 10/2008 |

(Continued)

OTHER PUBLICATIONS

U.S. Office Action from U.S. Appl. No. 12/804,172 dated Aug. 8, 2012 from the United States Patent and Trademark Office; 14 pages.

*Primary Examiner* — Vishal Pancholi
(74) *Attorney, Agent, or Firm* — Howard & Howard Attorneys PLLC

(57) ABSTRACT

System and method for monitoring hand hygiene of a user. The system includes a handheld electronic device for being carried by the user to generate device data such as location data. A portable dispenser assembly is worn by the user to dispense disinfectant fluid from a container in a plurality of dispensing events. The assembly includes an electronics unit that generates event data relating to the dispensing events. The assembly is separate from the handheld electronic device yet configured to communicate with the handheld electronic device. A monitoring system receives the device data and the event data relating to the dispensing events for evaluating the hand hygiene of the user.

20 Claims, 22 Drawing Sheets

Related U.S. Application Data is a continuation of application No. 13/464,527, filed on May 4, 2012, now Pat. No. 8,844,766, which is a continuation-in-part of application No. 12/804,172, filed on Jul. 14, 2010, now abandoned.

(60) Provisional application No. 61/270,866, filed on Jul. 14, 2009.

(51) Int. Cl.

| | | |
|---|---|---|
| *B67D 1/00* | (2006.01) | |
| *B67D 7/14* | (2010.01) | |
| *B67D 7/84* | (2010.01) | |
| *G06F 19/00* | (2018.01) | |
| *B05B 15/62* | (2018.01) | |
| *A61L 2/26* | (2006.01) | |
| *B05B 11/00* | (2006.01) | |
| *B05B 12/02* | (2006.01) | |
| *B65D 83/38* | (2006.01) | |
| *B65D 83/68* | (2006.01) | |
| *B65D 83/14* | (2006.01) | |
| *G08B 21/24* | (2006.01) | |
| *A45F 5/00* | (2006.01) | |
| *B65D 83/00* | (2006.01) | |
| *A45F 5/02* | (2006.01) | |
| *H04W 4/02* | (2018.01) | |
| *G16H 40/63* | (2018.01) | |
| *G16H 40/20* | (2018.01) | |

(52) U.S. Cl.
CPC ............ *A61L 2/26* (2013.01); *B05B 11/0037* (2013.01); *B05B 11/0059* (2013.01); *B05B 11/308* (2013.01); *B05B 11/3084* (2013.01); *B05B 12/02* (2013.01); *B05B 15/62* (2018.02); *B65D 83/0094* (2013.01); *B65D 83/386* (2013.01); *B65D 83/68* (2013.01); *B65D 83/7532* (2013.01); *G08B 21/245* (2013.01); *G16H 40/20* (2018.01); *G16H 40/63* (2018.01); *H04W 4/027* (2013.01); *A45F 2200/05* (2013.01); *A61L 2202/14* (2013.01)

(58) Field of Classification Search
USPC ......... 222/23, 36, 38, 52, 78, 100, 113, 162, 222/175, 181.1–181.3, 183.36
See application file for complete search history.

(56) References Cited

U.S. PATENT DOCUMENTS

| | | |
|---|---|---|
| 3,768,700 A | 10/1973 | Stranicky |
| 4,079,862 A | 3/1978 | Fegley |
| 4,223,804 A | 9/1980 | Morris et al. |
| 4,446,990 A | 5/1984 | Stevenson et al. |
| 4,620,646 A | 11/1986 | Crapser |
| 4,776,491 A | 10/1988 | Nitta |
| D304,677 S | 11/1989 | Nitta |
| D306,137 S | 2/1990 | Nitta |
| 4,962,491 A | 10/1990 | Schaeffer |
| 5,016,781 A | 5/1991 | Ten Wolde |
| 5,088,624 A | 2/1992 | Hackett et al. |
| 5,397,029 A | 3/1995 | West |
| D358,033 S | 5/1995 | Klump |
| 5,429,301 A | 7/1995 | Franks |
| D373,529 S | 9/1996 | Zogg et al. |
| 5,683,012 A | 11/1997 | Villaveces |
| 5,862,960 A | 1/1999 | Miller et al. |
| 5,927,548 A | 7/1999 | Villavaces |
| 5,945,910 A | 8/1999 | Gorra |
| 5,960,991 A | 10/1999 | Ophardt |
| 6,234,357 B1 | 5/2001 | Lewis |
| 6,236,317 B1 | 5/2001 | Cohen et al. |
| 6,283,334 B1 | 9/2001 | Mahaffey et al. |
| 6,305,580 B1 | 10/2001 | Chen |
| 6,375,038 B1 | 4/2002 | Daansen et al. |
| 6,392,546 B1 | 5/2002 | Smith |
| 6,550,476 B1 | 4/2003 | Ryder |
| 6,681,768 B2 | 1/2004 | Haaije de Boer et al. |
| 6,695,371 B1 | 2/2004 | Simkins |
| 6,727,818 B1 | 4/2004 | Wildman et al. |
| 6,779,689 B2 | 8/2004 | Flaig et al. |
| 6,845,888 B2 | 1/2005 | Verherbrugghen et al. |
| 6,882,278 B2 | 4/2005 | Winnings et al. |
| 6,883,563 B2 | 4/2005 | Smith |
| 6,975,231 B2 | 12/2005 | Lane et al. |
| 6,983,864 B1 | 1/2006 | Cagle |
| D532,698 S | 11/2006 | Pridmore et al. |
| 7,135,011 B2 | 11/2006 | Powers et al. |
| 7,163,101 B2 | 1/2007 | Harper |
| 7,178,696 B2 | 2/2007 | Larsen et al. |
| 7,179,696 B2 | 2/2007 | Chakravarthi et al. |
| D550,561 S | 9/2007 | Snyder et al. |
| 7,272,728 B2 | 9/2007 | Pierson et al. |
| 7,285,114 B2 | 10/2007 | Harper |
| 7,286,057 B2 | 10/2007 | Bolling |
| 7,293,645 B2 | 11/2007 | Harper et al. |
| 7,316,332 B2 | 1/2008 | Powers et al. |
| D563,789 S | 3/2008 | Mongeon et al. |
| 7,425,900 B2 | 9/2008 | Lynn et al. |
| 7,482,936 B2 | 1/2009 | Bolling |
| 7,721,920 B2 | 5/2010 | Ruiz de Gopegui et al. |
| 7,755,494 B2 | 7/2010 | Melker et al. |
| 7,757,895 B2 | 7/2010 | McGinley et al. |
| 7,825,812 B2 | 11/2010 | Ogrin et al. |
| 7,934,410 B2 | 5/2011 | Myers et al. |
| 7,978,083 B2 | 7/2011 | Melker et al. |
| D644,107 S | 8/2011 | Hirst et al. |
| 8,094,029 B2 | 1/2012 | Ortiz et al. |
| 8,100,841 B2 | 1/2012 | Rousso |
| 8,157,754 B2 | 4/2012 | Weintraub et al. |
| D660,180 S | 5/2012 | Floyd et al. |
| 2004/0020950 A1 | 2/2004 | Overbay |
| 2004/0069798 A1 | 4/2004 | Grey et al. |
| 2005/0247731 A1 | 11/2005 | Mathiez |
| 2006/0060554 A1 | 3/2006 | Garman |
| 2006/0062872 A1 | 3/2006 | Gebreselassie et al. |
| 2006/0218011 A1* | 9/2006 | Walker ............... A61J 7/0481 705/3 |
| 2006/0261084 A1 | 11/2006 | Grey et al. |
| 2007/0194048 A1* | 8/2007 | Teig .................. F21V 33/0076 222/113 |
| 2007/0229288 A1 | 10/2007 | Ogrin et al. |
| 2008/0047977 A1 | 2/2008 | Larsen et al. |
| 2008/0087560 A1 | 4/2008 | Kelly |
| 2008/0149126 A1 | 6/2008 | Abergel |
| 2008/0246599 A1 | 10/2008 | Hufton et al. |
| 2009/0091458 A1 | 4/2009 | Deutsch |
| 2009/0101676 A1 | 4/2009 | O'Connell et al. |
| 2009/0250371 A1 | 10/2009 | Nicoll |
| 2009/0263174 A1 | 10/2009 | Groh et al. |
| 2010/0084432 A1 | 4/2010 | Pelfrey |
| 2010/0094581 A1 | 4/2010 | Cagle |
| 2010/0117836 A1 | 5/2010 | Momen et al. |
| 2011/0011886 A1 | 1/2011 | Zaima et al. |
| 2011/0068930 A1 | 3/2011 | Wildman et al. |
| 2011/0076088 A1 | 3/2011 | Groh |
| 2011/0114650 A1 | 5/2011 | Boltshauser |
| 2011/0259359 A1 | 10/2011 | Groh et al. |
| 2012/0248140 A1 | 10/2012 | Iseri et al. |
| 2012/0291911 A1 | 11/2012 | Smith |
| 2013/0042865 A1 | 2/2013 | Monsees et al. |

FOREIGN PATENT DOCUMENTS

| | | | |
|---|---|---|---|
| WO | WO 2010 016909 | A1 | 2/2010 |
| WO | WO 2012 175983 | A1 | 12/2012 |

\* cited by examiner

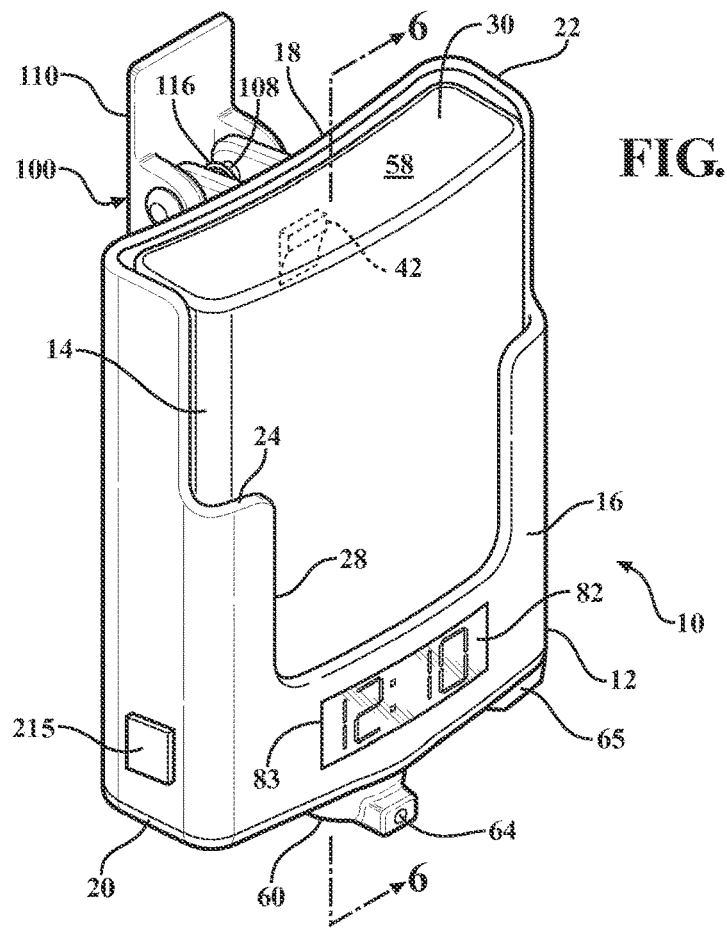
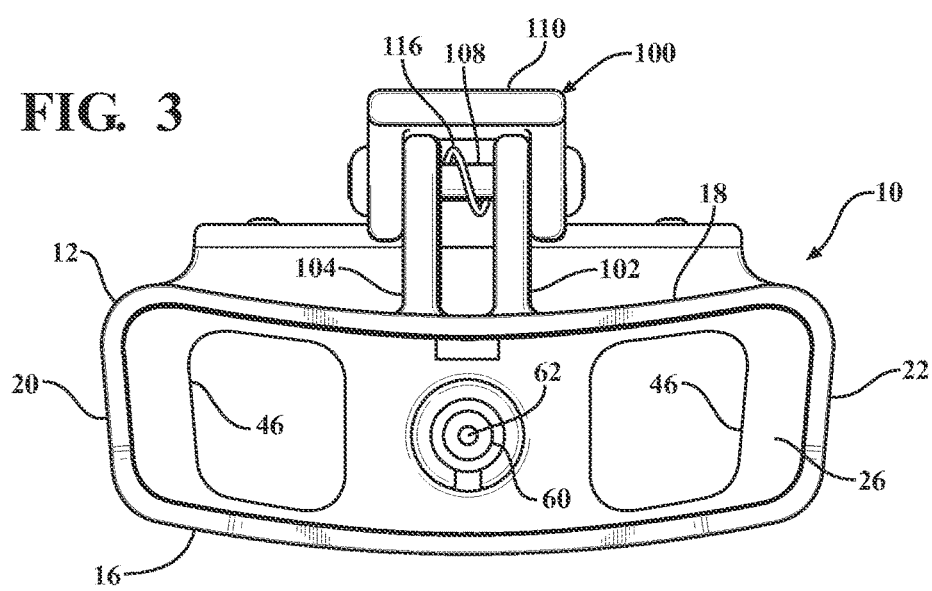

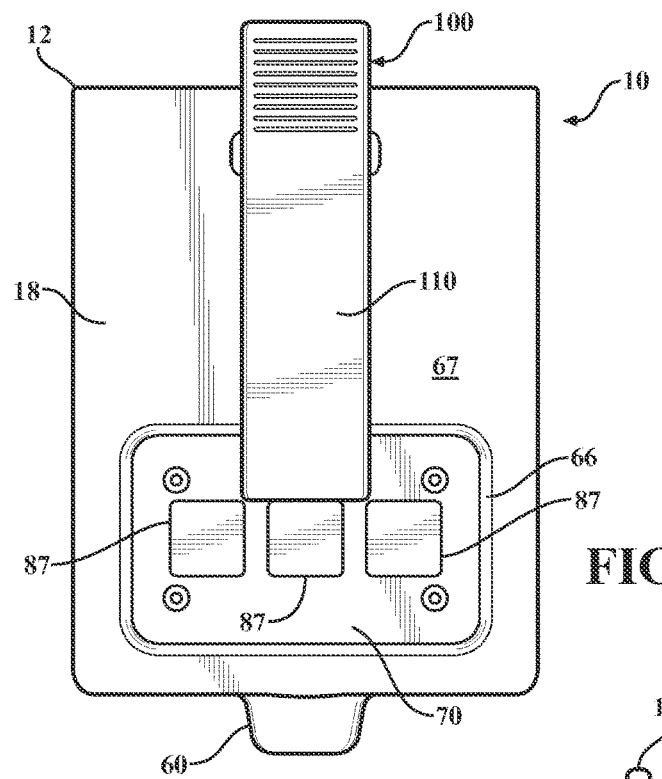
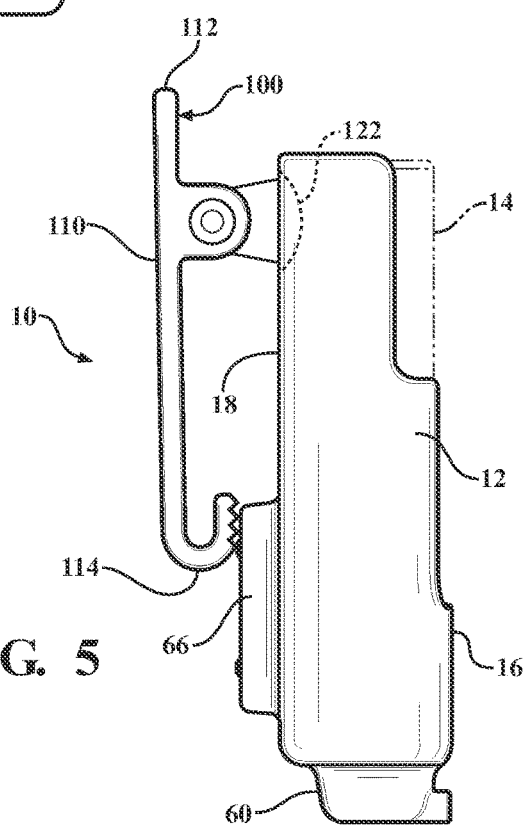
FIG. 4
FIG. 5

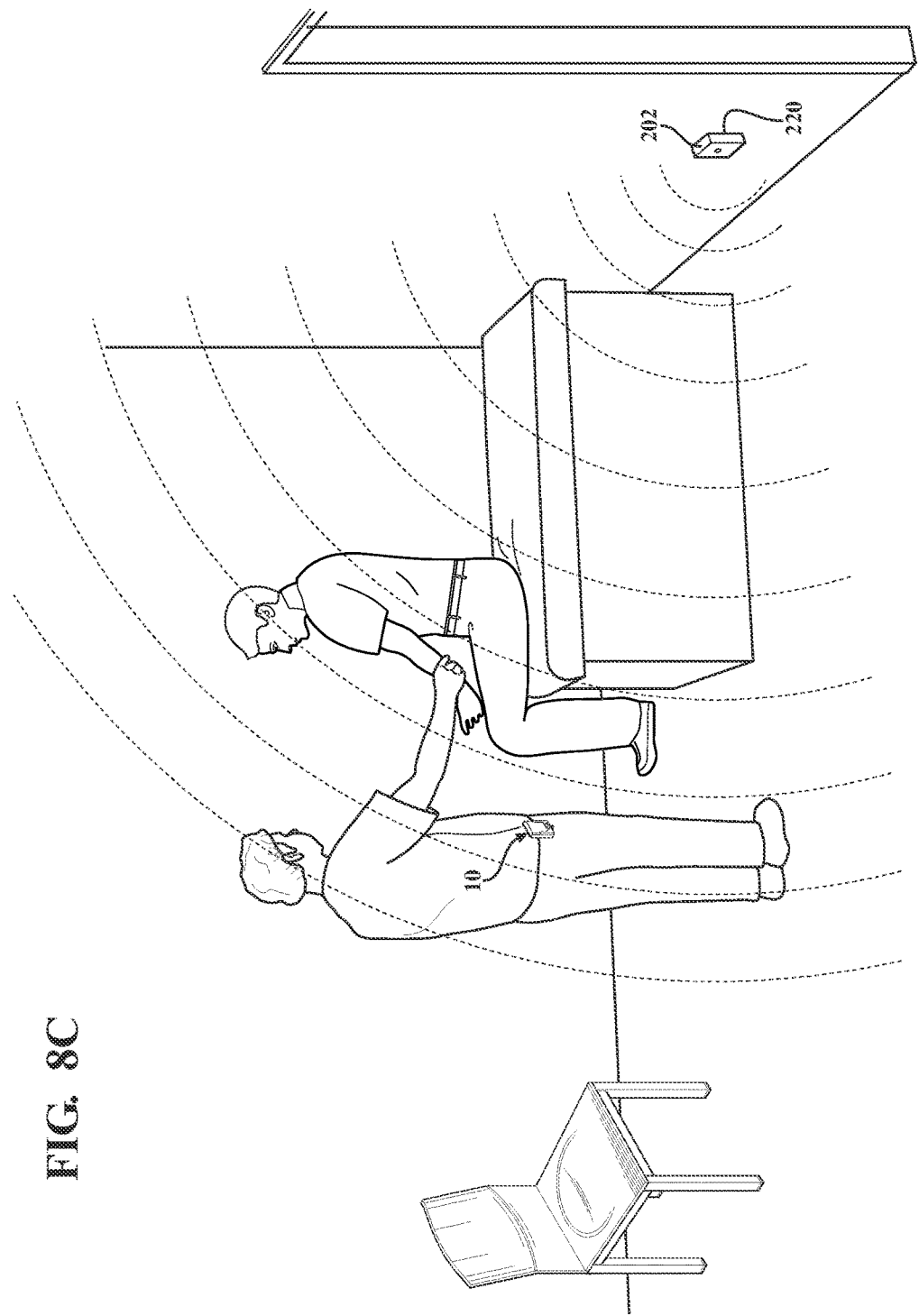

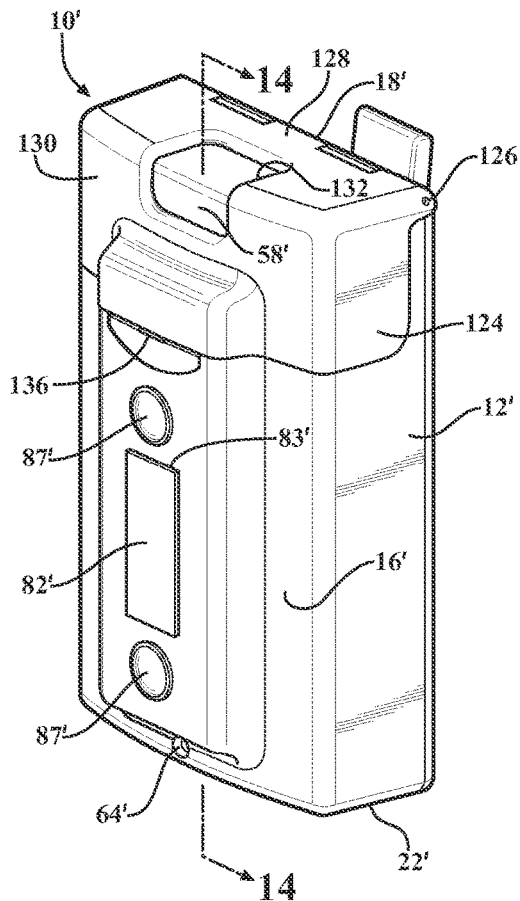
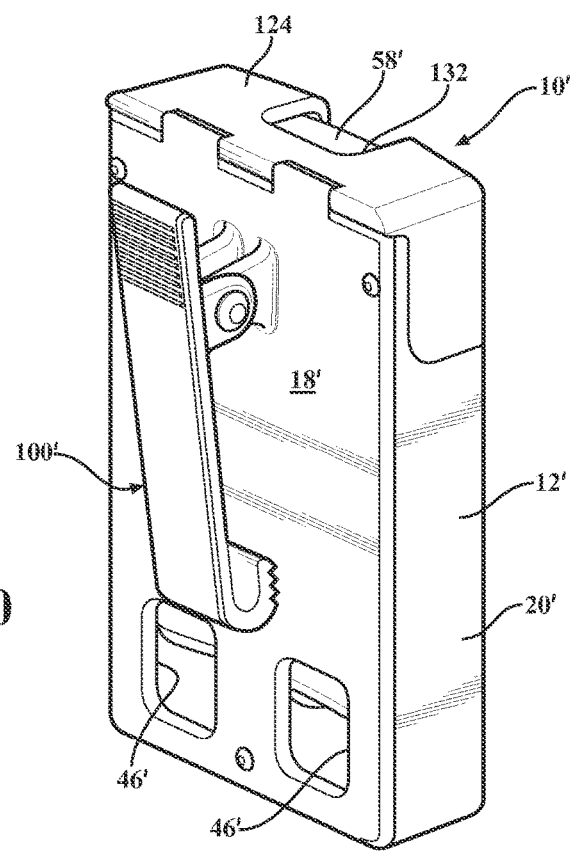

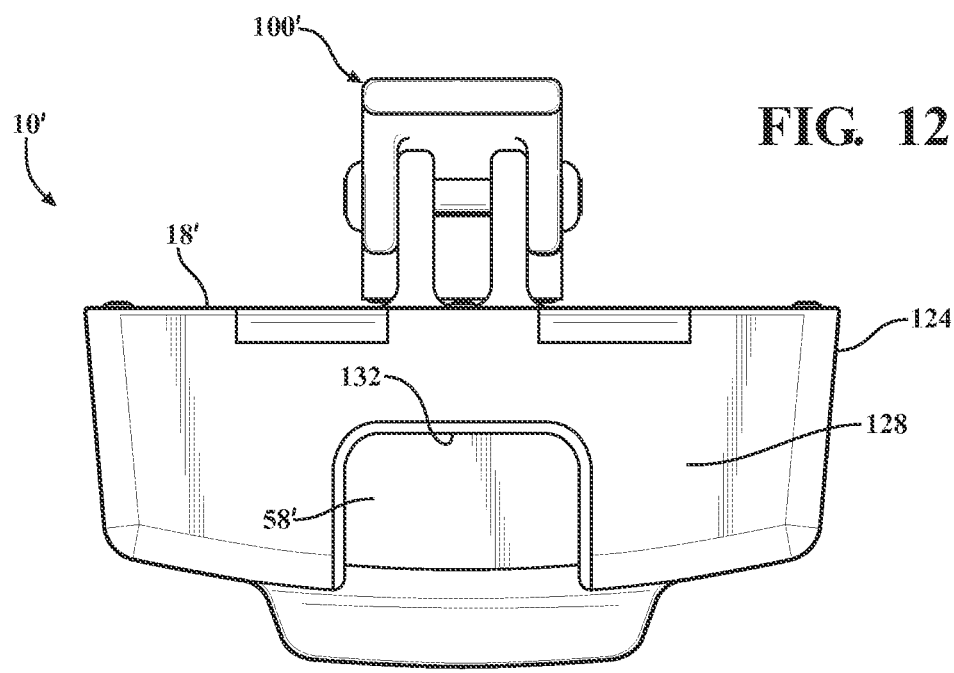
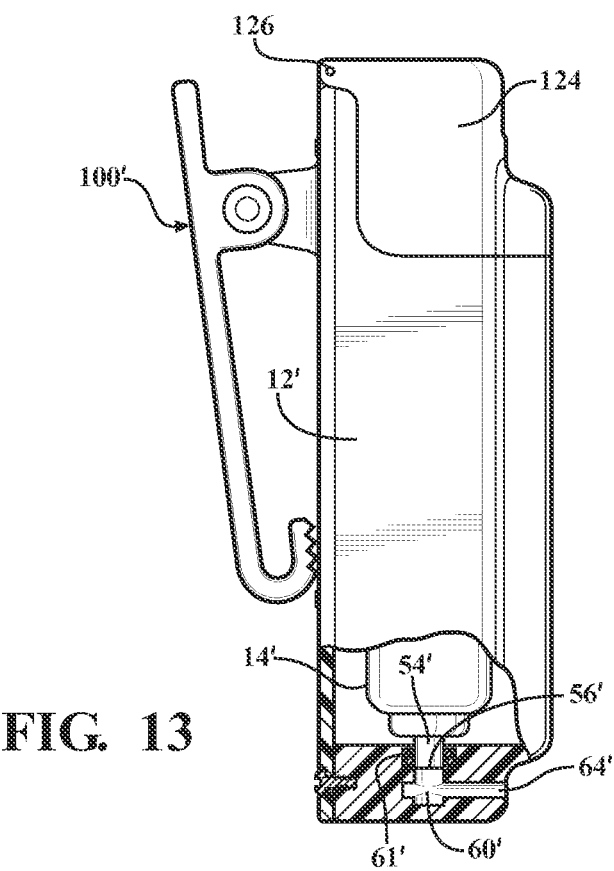

FIG. 19

Hand Hygiene Monitoring - User Management

| Dispenser ID | User Name | Facility | Floor | Unit | Classification | Shift |
|---|---|---|---|---|---|---|
| 1 | Doe, Michael | Oakdale | 3 | Cardiac | Doctor | Afternoon |
| 2 | Doe, William | Oakdale | 3 | Cardiac | Doctor | Afternoon |
| 3 | Doe, Jeffrey | Oakdale | 3 | Cardiac | Doctor | Afternoon |
| 4 | Doe, James | Oakdale | 3 | Cardiac | Doctor | Afternoon |
| 5 | Doe, David | Oakdale | 3 | Cardiac | Doctor | Morning |
| 6 | Doe, Harold | Oakdale | 3 | Cardiac | Doctor | Afternoon |
| 7 | Doe, Rajendra | Oakdale | 3 | Cardiac | Doctor | Afternoon |
| 8 | Doe, Mohammad | Oakdale | 3 | Cardiac | Doctor | Afternoon |
| 9 | Doe, Charles | Oakdale | 3 | Cardiac | Doctor | Afternoon |

Find User Name
Select a Name to Find

Save   Cancel

FIG. 21

SYSTEM AND METHOD FOR MONITORING HAND HYGIENE

RELATED APPLICATIONS

This application is a continuation-in-part of application Ser. No. 14/474,617, filed on Sep. 2, 2014, which is a continuation of application Ser. No. 13/464,527, filed on May 4, 2012, now U.S. Pat. No. 8,844,766, which is a continuation-in-part of application Ser. No. 12/804,172, filed on Jul. 14, 2010, now abandoned, which claims the benefit of U.S. Provisional Patent Application No. 61/270,866, filed on Jul. 14, 2009, the entire contents of all of which are hereby incorporated by reference.

FIELD OF THE INVENTION

The present invention relates to systems and methods for monitoring hand hygiene.

BACKGROUND OF THE INVENTION

Various infectious diseases such as SARS, Avian Flu, HIV, Herpes, MRSA, and most recently, H1N1 influenza, have had a significant impact on the world population. With the rise of world travelers, such infectious diseases are able to spread more readily from region-to-region and country-to-country, and this pace will only continue to accelerate. Early detection of such infectious diseases and prevention of transmittal are two ways to prevent a widespread epidemic. Also, these infectious diseases are capable of being spread in medical facilities, restaurants, and other public facilities. But in order to stop transmission, the infection must be eradicated at the most widely noted point of transmission. It is well-known that the greatest medium of communication of any bacteria or influenza is through touch. Primarily, this touch is by the hands. Therefore, cleansing the hands frequently and at the appropriate time is essential in the prevention of infectious diseases, most importantly in hospitals where bacteria and pathogens are abundant and where medical practitioners are constantly exposed to such pathogens through contact with patients and the general public.

One method that is available to destroy illness causing pathogens before infection can set in or be transmitted is the use and application of products including anti-microbacterial agents with ethyl alcohol gels, foam, or liquids. Such products are readily available, are effective in eradicating infectious pathogens from spreading, and kill bacteria upon contact. However, merely having these bacteria killing substances are insufficient. The product must be used, used often, and more importantly used at the correct time. As such, the product must be readily available and the user must use the product at the correct time. Thus, for any disinfecting product to work, the disinfecting substance must be effective, the user must have immediate and convenient access to a device that dispenses the product, and most importantly the disinfecting substance must be applied at the appropriate time.

Currently, medical facilities have multiple locations where medical practitioners can properly cleanse their hands with soap and water. In addition, many medical facilities have stations with antibacterial dispensing containers mounted to the walls. Further, medical practitioners may carry relatively small canisters in their pockets to sterilize their hands prior to each patient examination in order to prevent the transmission of infectious disease. The general public has fewer opportunities to properly and constantly cleanse their hands, with the most common available means being gel pump soap systems found in restrooms of stores and restaurants. Though helpful, none of these methods have proven to be truly effective. In hospitals, the location for properly cleansing the hands with antibacterial soap is not always immediately available. And even if they are available, frequent washing of the hands causes hands to become dry and chaffed resulting in discomfort to both the medical practitioner and the patient.

In the case of gel, liquid, and foam hand sanitizing stations, it must be readily available when the medical practitioner needs or wants to use it. Even if available, often times the medical practitioner finds that the disinfectant at the stations is empty, therefore, constant monitoring and refilling are required. The small canisters are somewhat effective, however, medical practitioners tend to set them down whereby misplacing them. In order for the cleansing agent to be effective, the method of cleansing the hands within the hospital or in public locations must be convenient and readily accessible when the user thinks of the need for use.

SUMMARY OF THE INVENTION

In one embodiment, the invention provides a system for monitoring hand hygiene that comprises a handheld electronic device and a portable dispenser assembly. The handheld electronic device generates device data. The portable dispenser assembly is worn by the user to dispense disinfectant fluid from a container in a plurality of dispensing events. The assembly is separate from the handheld electronic device. The assembly includes a main housing defining a cavity for receiving the container. A nozzle defines an inlet for receiving the disinfectant fluid from the container and an outlet for directing the disinfectant fluid toward the user. An electronics unit is coupled to the main housing to generate event data relating to the dispensing events. A monitoring system receives the device data and the event data relating to the dispensing events for evaluating hand hygiene of the user.

In another embodiment, a method is provided for monitoring hand hygiene by a user. The method comprises providing a portable dispenser assembly for being worn by the user to dispense disinfectant fluid from a container in a plurality of dispensing events. The assembly includes a main housing defining a cavity for receiving the container. A nozzle defines an inlet for receiving the disinfectant fluid from the container and an outlet for directing the disinfectant fluid toward the user. An electronics unit is coupled to the main housing to generate event data relating to the dispensing events. The method further includes collecting, at a monitoring system, the event data generated by the electronics unit and device data generated by a handheld electronic device. The handheld electronic device is separate from the portable dispenser assembly and configured to communicate with the electronics unit.

In these embodiments, the portable dispenser assembly is made readily available to a user, such as a medical practitioner or an individual consumer, by being attachable to their person. As a result, the user is not constantly looking for a hand washing station or wall-mounted disinfectant fluid dispenser units, which are often empty even if located. Having the medical practitioner wear the portable dispenser assembly also serves as a visual reminder and assurance for the patient to ensure and witness the use of the disinfectant fluid before examination. As a result, the transmission of infectious diseases within medical facilities and among the general public is greatly reduced, thereby lowering medical costs and reducing inpatient stays.

BRIEF DESCRIPTION OF THE SEVERAL VIEWS OF THE DRAWINGS

Advantages of the present invention will be readily appreciated as the same becomes better understood by reference to the following detailed description when considered in connection with the accompanying drawings wherein:

FIG. 1 is a perspective view of a dispenser assembly according to a first embodiment of the invention;

FIG. 3 is a top view of the main housing for the dispenser assembly in a first embodiment of the invention;

FIG. 4 is a rear view of the dispenser assembly in a first embodiment of the invention;

FIG. 5 is a side view of the dispenser assembly in a first embodiment of the invention;

FIG. 8C is a fragmentary perspective view of a room including an electronic emitter coupled to a power source and emitting a signal for sensing by the dispenser assembly;

FIG. 9 is a front perspective view of a dispenser assembly in a second embodiment of the invention;

FIG. 10 is a rear perspective view of the dispenser assembly in a second embodiment of the invention;

FIG. 12 is a top view of the dispenser assembly in a second embodiment of the invention;

FIG. 13 is a side view, partially cut away, of the dispenser assembly in a second embodiment of the invention;

FIGS. 18-22 include screen shots of software for monitoring and reporting dispensing events.

DETAILED DESCRIPTION OF THE INVENTION

Figure 2:
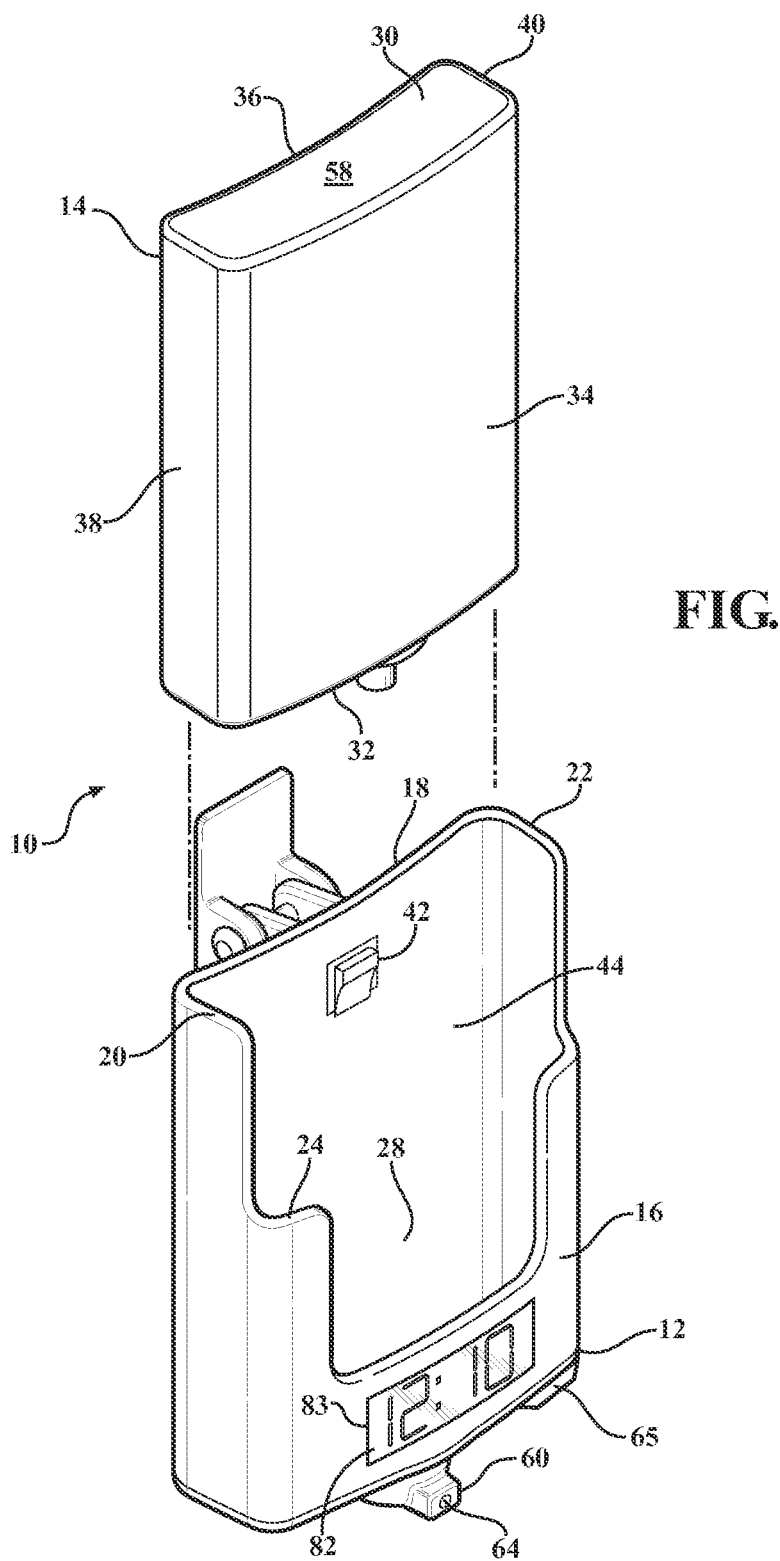
FIG. 2 is an exploded perspective view of the dispenser assembly in a first embodiment of the invention including a main housing and a canister.

Referring to FIGS. 1 through 6, a dispenser assembly, generally shown at 10, according to a first embodiment of the invention includes a main housing 12 and a container 14 (also referred to as a canister). The main housing 12 includes a front wall 16, a back wall 18, and side walls 20, 22 each extending between the front wall 16 and the back wall 18. The front wall 16 and a portion of the side walls 20, 22 in one embodiment are cut out to form an upper edge 24 having an irregular shape. In one embodiment, each of the front 16 and back 18 walls is generally curved or arcuate. The main housing 12 also includes a bottom wall 26. The front wall 16, the back wall 18, the side walls 20, 22, and the bottom wall 26 together define a cavity 28.

It is contemplated that the particular shape, size, and configuration of the main housing 12 may vary. In one embodiment, the main housing 12 may be a claw-type holder. The main housing 12 can be produced from any of numerous materials including, but not limited to, metal or a thermoplastic material. The thermoplastic material may be an anti-bacterial resin such as IonArmour, Masterbatch, or any of a variety of commercially available anti-bacterial resins.

The container 14 is received within the cavity 28 of the main housing 12. The container 14 includes an upper wall 30 and a lower wall 32. The container 14 also includes four sides 34, 36, 38, 40 each extending between the upper 30 and lower 32 walls. In one embodiment, the contour of the front 34 and back 36 sides of the container 14 is complementary to the curvature of the front 16 and back 18 walls of the main housing 12 to ensure a proper fit when the container 14 is placed inside the cavity 28 of the main housing 12. It is, however, appreciated that the container 14 may be any of numerous shapes including, but not limited to, cylindrical-shaped, oval-shaped, or crescent-shaped.

The container 14 is secured to the main housing 12 to prevent the inadvertent release of the container 14. The main housing 12 includes a tab 42 formed along a forward surface 44 of the back wall 18. The tab 42 engages a recessed portion formed along the back side 36 of the container 14 so that the container 14 is securely held within the cavity 28 of the main housing 12. The container 14 is secured in alternative embodiments with portions that may be interference fit or by using other conventional retaining devices.

When the container 14 is empty, it is necessary to replace the existing container 14 with a new container 14. In order to release the container 14, a user inserts a finger or a similarly-shaped object through at least one aperture 46 formed along the bottom wall 26 of the main housing 12 and pushes against the container 14 to disengage the tab 42 from the recessed portion. As a result, the container 14 is no longer secured to the main housing 12. The tab 42, which is generally tongue-shaped, includes a bottom portion that is attached to the back wall 18 such that the tab 42 flexes back when the container 14 is removed from the main housing 12.

In another embodiment, the side walls 20, 22 of the main housing 12 could be formed at a height lower than that of the container 14 which allows the user to grab the container 14 for easy removal and replacement. In other embodiments, one or both of the side walls 20, 22 of the main housing 12 have a depressible finger or tab (not shown) that is generally tongue-shaped and hinged to the main housing 12 to engage an outer surface of the container 14. Upon depressing the tab, a protrusion disposed at a distal end of the tab engages the outer surface to raise the container 14 in the main housing 12 and allow the user to grasp the container 14 and lift it out of the main housing 12.

The container 14 includes an interior 48 that is configured to contain a fluid. The fluid may include liquids, gels, lotions, gases, and foams, such as disinfectant fluids (e.g., sanitizers), and other fluids and fluid-like substances. The container 14 may be pressurized or non-pressurized depending upon the particular fluid that is utilized.

Figure 6:
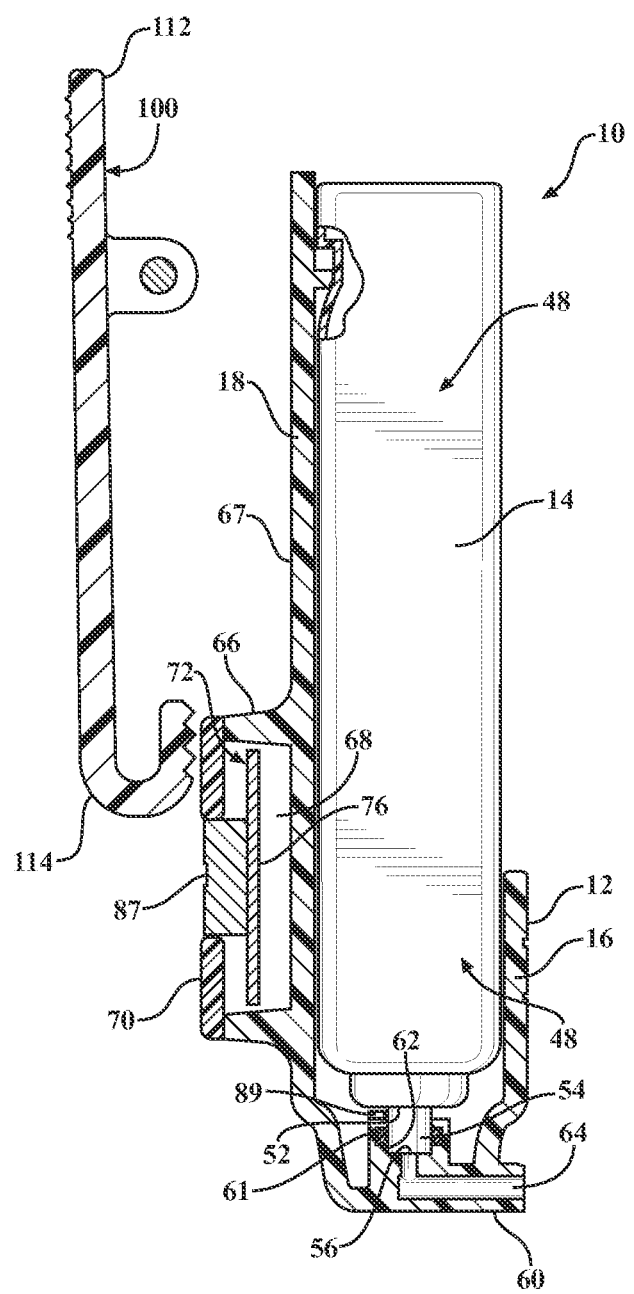
FIG. 6 is a cross-sectional view taken along line 6-6 in FIG. 1 of the dispenser assembly in a first embodiment of the invention.

Referring specifically to FIG. 6, the container 14 in one embodiment includes an intake tube (not shown), a pump mechanism 52, and a stem 54 disposed within the interior 48 for selectively forcing fluid out of the container 14, as is well-known to those of ordinary skill in the art. The stem 54 is in fluid communication with the interior 48 of the container 14 such that fluid is able to selectively exit the container 14 through an open end 56 of the stem 54. The container 14 includes a depression button 58 (shown in FIG. 1 as a surface) which is pressed downwardly by a user to activate the pump mechanism 52 and force the fluid out of the container 14 through the open end 56 of the stem 54. In some embodiments the container 14 is an aerosol container in which the pump mechanism 52 is further defined as a valve that is opened by depressing the container 14 relative to the stem 54 against the bias of a valve spring (not shown). Such valves are conventional in the aerosol dispensing container arts and are not described in detail herein. See, for example, the valve system and container in U.S. Pat. No. 6,978,916, hereby incorporated by reference.

Referring again to FIG. 6, the main housing 12 includes a nozzle 60 extending out from the bottom wall 26. The nozzle 60 is in fluid communication with the stem 54 to selectively eject the fluid from the dispenser assembly 10. The nozzle 60 includes an inlet 62 that is coupled to the open end 56 of the stem 54 to transfer fluid from the interior 48 of the container 14 to the nozzle 60. The nozzle 60 also includes a fluid discharge aperture 64 through which fluid is expelled upon activation of the dispenser assembly 10. It is further appreciated that in such embodiments the stem 54 is biased back to its normal position by the valve spring (not shown), as is conventional in the art. Since the stem 54 is fixed in position in the nozzle 60, this bias results in the container 14 be biased upwardly to be readied for subsequent use.

A seal 61 is disposed in a groove (not separately numbered) in the nozzle 60. The seal 61 contacts and seals against the stem 54 when the stem 54 of the container 14 is positioned in the nozzle 60. The nozzle 60 is integral with the main housing 12. Alternatively, the nozzle 60 may be separate from the main housing 12 and have wings (not shown) that act as tabs which allow the nozzle 60 to be removed from the main housing 12 and replaced. In alternative embodiments, the nozzle 60 could be screwed into the main housing 12 and be unscrewed to allow the nozzle 60 to be replaced or cleaned as required.

The container 14 is metered. In some embodiments, a mechanism for metering a dose of fluid (not shown) is located within the container 14. In these embodiments, the mechanism comprises an internal assembly as is well known to those skilled in the art for metering out each dose of fluid prior to dispensing so that actuation of the container 14 results in the metered dose being dispensed. If the container 14 is not actuated properly to dispense the entire dose, a partial dose may be dispensed. In this case, a dispensing event will not be recorded. Still, another full dose is metered out for the next dispensing event. In other embodiments, such as when using pump actuated containers, the meter is set such that a full dose of fluid is dispensed only when the depression button 58 of the container 14 is fully depressed. Fully depressing the container 14 resets the container 14 to ensure dispensing of fluid. In either case described above, if the container 14 is not fully actuated to dispense a full dose, in some embodiments, the user will not receive credit from the monitoring system, described below, for a dispensing event.

The quantity of fluid in the container 14 and the specific metered dosage thereof may be calibrated such that the proper amount is dispensing every time and depending on the usage rate the user will only have to replace the container 14 on a periodic basis.

The dispenser assembly 10 includes a metering adjustment device which ensures that each dispensing of the fluid can be properly adjusted and metered to prevent either too much or too little fluid from being dispensed at one time. The metering adjustment device may be a material that is positioned at the bottom of the main housing 12 that limits how far the container 14 can be depressed, thereby controlling the amount of fluid that is dispensed. In another embodiment, the metering adjustment device includes an adjustable threaded stopper wherein the position of the stopper can be adjusted to ensure that the container 14 bottoms out against the stopper at the right metering position.

The dispenser assembly 10 includes an electric or mechanical counter (not separately numbered) that counts the number of times that fluid has been dispensed (e.g., the number of dispensing events of the dispenser assembly 10). Each time a new container 14 is inserted into the main housing 10, the counter resets and begins to count the number of times that the dispenser assembly 10 has been used. Once the counter reaches a predetermined number, a warning alert is activated (visual, audible, or tactile) to notify the user that it is time to replace the container 14. In the alternative, the warning alert may include a device that is built into the container 14 that produces an audible sound such as a spitting sound when the fluid level is low.

Once the fluid has run out, the empty container 14 is replaced with a full container 14. In an alternative embodiment, the container 14 may include a cover selectively covering a refill opening in a top of the container 14. To refill the container 14, the cover is moved out of the way and fluid is added to the container 14 from a master container via the refill opening.

In one embodiment, a light source 65 is disposed along the bottom wall 26 of the main housing 12, as shown in FIG. 1. The light source 65 may be an ultraviolet, infrared, or similar light source which allows a user to check the effectiveness of the dispenser assembly 10 and associated dispensing events by shining a light onto the area of fluid application and subsequent sanitization to allow the user to ensure the cleanliness of the area of fluid application (e.g., the sanitized area).

Referring to FIGS. 4 through 6, the dispenser assembly 10 includes a flange 66 formed along an outboard surface 67 of the back wall 18 of the main housing 12. The flange 66 and the back wall 18 of the main housing 12 define a chamber 68. It is appreciated that the particular location of the chamber 68 relative to the main housing 12 may vary. The chamber 68 is selectively closed by a removable cover 70. The cover 70 may be sealed or unsealed.

Figure 7:
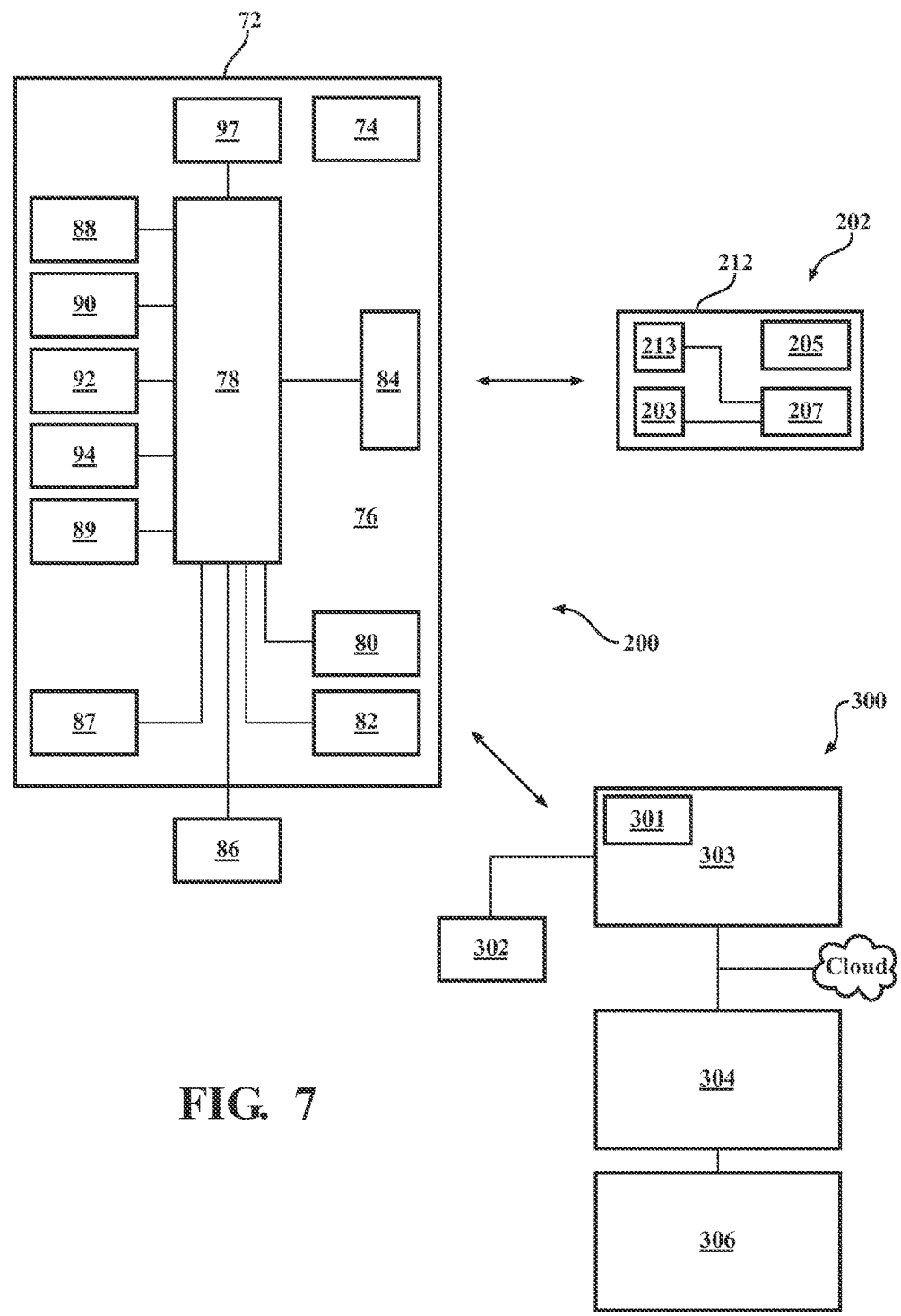
FIG. 7 is a schematic diagram of an electronic reminder alert and data collection system and monitoring system.

Referring to FIGS. 6 and 7, an electronics unit, generally indicated at 72, is disposed within the chamber 68. The electronics unit 72 generates an alarm (also referred to as a reminder alert) for the user and communicates information to the user regarding the dispenser assembly 10. The electronics unit 72 also collects and transmits data associated with the user and/or dispensing events through a wired or wireless connection.

The electronics unit 72 includes a power source 74 positioned in the chamber 68 for providing power. The power source 74 is preferably a rechargeable battery 74. In some embodiments the container 14 includes the power source 74 so that when the container 14 is refilled, the container battery 74 can also be recharged. In those embodiments, the battery 74 from the container 74 is electrically connected to the electronics unit 72 to power the electronics unit 72.

A printed circuit board 76 is connected to the power source 74 for distributing power. A controller 78 is operatively connected to the power source 74 (not shown—connection is through the printed circuit board 76). The controller 78 includes a microprocessor. The controller may be a microcontroller available from Microchip Technology of Arizona, model no. PIC 18F46J50.

A sensor 80 for detecting signals such as a wireless activation signal is operatively connected to the controller 78. The sensor 80 is operatively connected to the controller 78 to send signals to the controller 78. The sensor 80 includes an antenna in some embodiments for receiving signals. One such antenna may be a grounded line planar antenna sold under the tradename SPLATCH, Model No. 433-SP2 sold by Linx Technologies of Merlin, Oreg.

A transceiver 82 is operatively connected to the controller 78. The transceiver 82 transmits/receives signals to/from external devices and/or transceivers (transmitter/receiver). It should be understood that the sensor 80 could be the antenna of the transceiver 82 or could be a separate sensor/receiver. The transceiver 82 may be a RF Module Transceiver Model No. TRM-433-LT, sold by Linx Technologies of Merlin, Oreg. Such a transceiver provides for bidirectional wireless transfer of serial data, control, or command information in the 260-470 MHz frequency range. This transceiver is capable of generating 10 dBm from a 50-ohm load and achieves a receiver sensitivity of typically-112 dBm.

A memory 84 communicates with the controller 78 to transfer and/or store data associated with the user and dispensing events. The data may include a unique identifier associated with the dispenser assembly 10 and the user that is stored in the memory 84 and date, time, and/or location information for dispensing events. The data may be transmitted from the transceiver 82 of the dispenser assembly 10 by a wireless connection, e.g., radio waves (such as Bluetooth, Zigbee or Wi-Fi), infrared, or a wired connection, such as an Ethernet connection or USB connection. Other types of data transmission are also contemplated.

A display 86 (shown in FIG. 1) is operatively connected to the controller 78. The display 86 displays alphanumeric characters, graphics, images, and the like through a screen window 83 formed along an outer surface of the main housing 12. The display 86 may be LED, LCD, or other types of displays. In one embodiment, the display 86 is positioned along the front wall 16 of the main housing 12. It is, however, appreciated that the display 86 may be found in any of various locations on the main housing 12. Referring back to FIG. 7, the dispenser assembly 10 also includes a speaker 88, a vibrating mechanism 90, and a clock 92 each operatively connected to the controller 78. The display 86 can display the date and time, advertisements, the name of the medical facility, the name of the practitioner or user of the dispenser assembly 10, or the name of the provider of the disinfectant fluid, or any combination of items. The display 86, speaker 88, and vibrating mechanism 90 act as visual, audible, and tactile annunciators of the electronics unit 72.

At least one button 87 is coupled to the printed circuit board 76. In some embodiments, the button 87 extends through the removable cover 70. The button 87 operates as an input to the controller 78. The button 87 may actuate a switch or other electronic signaling device to provide input to the controller 78. Other input devices could also be used such as a touch-sensitive interface, speech recognition input device, delta-p transducer/sensor, flow sensor, resistive and/or capacitive sensors, and the like.

The electronics unit 72 provides an alarm that reminds the user to dispense disinfectant at certain times or at certain locations. The alarm could be a light (i.e., a visual alarm), an audible alarm from the speaker 88, a vibration initiated by the vibrating mechanism 90 (i.e., a tactile alarm), or a combination of these alarms. Settings in some embodiments could be established in which the alarm is only turned off when the disinfectant fluid has been dispensed. In certain preferred embodiments, the alarm is only turned off when the container 14 has been fully depressed and the properly metered amount of fluid has been expelled. Administrators and/or users of the system have the ability to select which one or more of the light (or other visual alarm), audible alarm, and vibration to use for the alarm. But at least one of the alarms must remain available during use. Only an authorized administrator would have the ability to deactivate all three of the alarms for a user. The alarm is activated when the controller 78 generates a reminder signal and transmits the reminder signal to the annunciator 86, 88, 90 to actuate the annunciator 86, 88, 90.

In some embodiments, the alarm may be staged or sequenced by first having a tactile alarm for a predetermined period of time (which could be delayed a predetermined period of time before being activated as described further below) and then escalating to an audible alarm after the predetermined period of time elapses (the second, audible alarm, could also be delayed before being activated a second predetermined period of time after the first tactile alarm is terminated). By using a tactile alarm first, the user is made aware of the alarm but the alarm is less annoying to others when compared to an audible alarm.

Figure 8A:
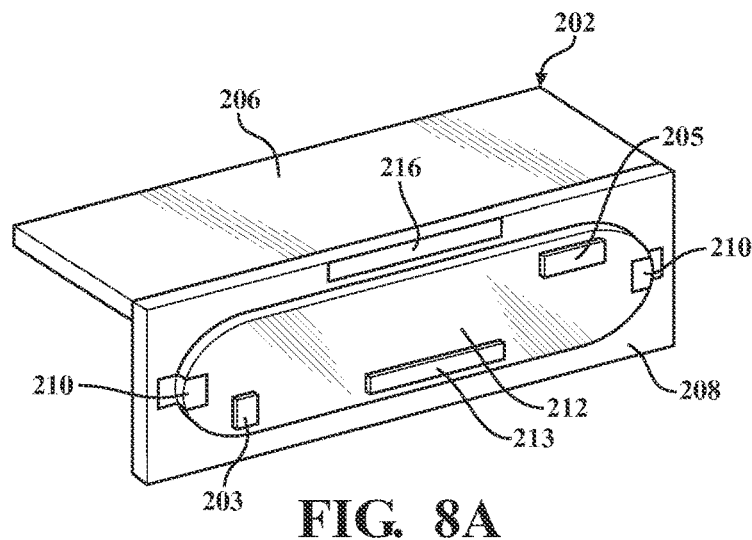
FIG. 8A is an oblique view of an electronic emitter assembly for emitting a signal to be received by the dispenser assembly.

Referring to FIGS. 7 through 8c, an electronic reminder and data collection system 200 for producing the alarm includes the dispenser assembly 10 and an electronic emitter, generally indicated at 202. The electronic emitter 202 includes a transceiver 203 that emits the activation signal, which may be an infrared signal, a radio frequency (RF) signal, other electrical signal, or any combination thereof. In some embodiments, the transceiver 203 of the electronic emitter 202 is the same as the transceiver 82 of the electronics unit 72. Thus, the transceiver 203 could also include an antenna such as the same grounded line planar antenna sold under the tradename SPLATCH, Model No. 433-SP2 sold by Linx Technologies of Merlin, Oreg.

Figure 8B:
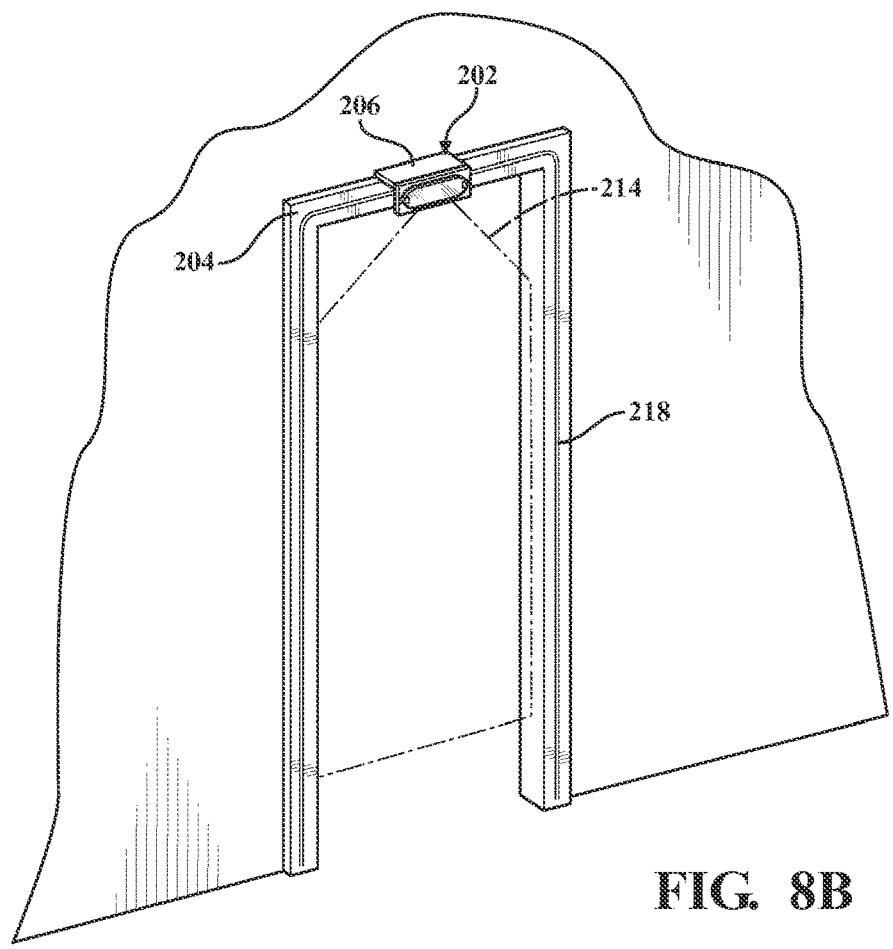
FIG. 8B is a front view of a door including the electronic emitter assembly fixedly mounted to a door jamb to create an electronic curtain in a passageway underneath the door jamb.

In one embodiment, the electronic emitter 202 is adapted to be secured to a door jamb 204, as shown in FIG. 8B. The electronic emitter 202 includes a top flange 206 mounted to the door jamb 204 and a backing member 208. A retainer flange 210 extends out from the backing member 208 on both ends of the backing member 208. A printed circuit board 212 is mounted to the retainer flange 210.

The electronic emitter 202 includes a detector 213 mounted to the printed circuit board 212. The detector 213 is oriented to project an infrared beam downward to form a curtain 214. The curtain 214 (also referred to as a beam) covers a substantial portion of the passageway underneath the door jamb 204. The infrared curtain 214 detects a user entering or exiting a room or area. When detected, the detector 213 sends a signal to the transceiver 203, which then generates and emits the activation signal to the dispenser assembly 10 to prompt a dispensing event. Communication between the electronic emitter 202 and the electronics unit 72 is generally shown by a double arrow in FIG. 7.

The detector 213 can be hard wired to the transceiver 203 on the printed circuit board 212 or connected wirelessly to the transceiver 203. The transceiver 203 can be placed at a separate, spaced location from the detector 213. In some embodiments an emitter controller 207 is operatively connected to the detector 213 and the transceiver 203 to process signals from the detector 213 and instruct the transceiver 203 to emit the activation signal in response to detecting the user. The emitter controller 207 may be the same as the controller 78, which in some embodiments is the microcontroller available from Microchip Technology of Arizona, model no. PIC 18F46J50.

In some embodiments, the detector 213 is a motion sensor. The detector 213 may be a passive infrared sensor that senses radiation changes. In other embodiments, the detector 213 is a radio frequency identification (RFID) reader. When the detector 213 is a RFID reader, a corresponding RFID tag 215 (see FIG. 1) is attached to the dispenser assembly 10. The RFID reader detects the user when the RFID reader receives a signal from the RFID tag 215 upon the user passing within a predetermined proximity of the RFID reader. The RFID tag 215 could also be the same RFID tag used for entry into the facility, e.g., the hospital, office, etc.

The RFID reader is operatively connected to the emitter controller 207 in the embodiments in which the emitter controller 207 is present. The emitter controller 207 has a processor. A memory (not shown) communicates with the emitter controller 207. The memory stores values with each value corresponding to a category of RFID tag types (e.g., a look-up table) and the RFID tag unique identifiers for each assigned user that falls in the categories.

In yet other embodiments, the detector 213 includes both an infrared sensor and a RFID reader. The infrared sensor could be a passive infrared sensor that senses radiation changes such as when the user passes the detector 213 and the RFID reader would detect the RFID tag attached to the dispenser assembly 10.

The emitter controller 207 may be configured to prompt the dispensing event for only certain categories. For instance, doctors may be assigned RFID tags with unique identifiers that fall in a different category than nurses, which is further different than visitors. Accordingly, the emitter controller 207 will be programmed to distinguish between doctors, nurses, visitors, etc. and may only prompt a dispensing event for the nurses, or for only the visitors. In other words, the emitter controller 207 may instruct the transceiver 203 to only emit the activation signal upon detecting certain people's RFID tags, while ignoring others. As a result, the dispenser assemblies 10 can be customized based on user type or other categories. In variations of this embodiment the transceiver 203 may emit unique activation signals for different categories of users thus only activating the alarm for specified users.

In other embodiments, the emitter controller 207 may be configured to produce activation signals through the transceiver 203 according to different frequencies so that different categories of individuals can be selectively alerted. In this case, one transceiver 203 could emit a signal at 433 MHz for one category of individuals and another transceiver 203, located in a different area, could emit a signal at 533 MHz. In this embodiment, the controller 78 of the dispensing assembly 10 is programmed to recognize the corresponding frequency emitted from the emitter 202 that is associated with a particular user type, while ignoring others. This is especially useful for placing electronic emitters 202, for example, in a hallway to alert people transporting individuals to sanitize their hands, without alerting doctors frequently traveling down the same hallways. This provides the system with the ability to selectively activate one user's alarm on their dispenser assembly 10, without activating a second user's alarm, even when they pass by the same electronic emitter 202.

In some embodiments, the sensor 80 of the dispenser assembly 10 is a RFID reader that reads RFID tags (not shown) mounted to the patient that identifies the patient. The RFID tags can also be mounted to the door jamb 204, or walls, surfaces, or other locations. The sensor 80 may also be an infrared (IR) sensor, a radiofrequency (RF) sensor (e.g., radio antenna), an ultrasonic sensor, or other wireless sensor.

When a user wearing the dispenser assembly 10 walks through the curtain 214, or is otherwise detected, the detector 213 sends a detection signal to the emitter controller 207 (or directly to the transceiver 203 in certain embodiments). In response, the transceiver 203 transmits the activation signal to the dispenser assembly 10. The activation signal may be a wireless signal such as a RF signal which may further be focused and/or pulsed. The combination of the two signals, i.e., detection and activation, with unique attributes prevents inadvertent reception of the activation signal by other dispenser assemblies 10 in the general area that are not intended to receive the activation signal. The activation signal can be focused by shielding errant transmission of the RF signal using conventional signal blocking techniques. The output power of the RF signal can be attenuated to reduce the range of coverage to further prevent inadvertent activation of other dispenser assemblies 10 in the general area that are not intended to be activated by the electronic emitter 202. False signals can further be avoided with signal frequencies that result in more controlled or restricted emission. This, for instance, can reduce penetration of the RF activation signal through walls or other barriers. Additionally, directional antennae and signal strength can be used to focus the RF activation signal.

Downward and inward (e.g., into the room or located inside the room away from the door) projection of the activation signal by the electronic emitter 202 further prevents a false alarm. For instance, if the curtain 214 is used to detect the user, the user must actually enter the room and break the curtain 214 to initiate the alarm. In some embodiments, the activation signal may be continuously transmitted foregoing the need for the detector 213. However, with the detector 213, the activation signal is not required to be continuously transmitted and is only transmitted upon the detector 213 detecting the user or the user worn dispenser assembly 10, e.g., via RFID tag 215.

Once the dispenser assembly 10 enters the room and receives the activation signal from the emitter 202, as long as the transceiver 82 stays in signal contact with the activation signal, the controller 78 will lock out further prompting from the emitter 202 and temporarily disable alerting the dispenser assembly 10. The controller 78 is programmed that once the dispenser assembly 10 is out of signal range from that particular emitter 202 for a predetermined period of time the controller 78 resets to allow further prompting from the same emitter 202. The controller 78 can be programmed in various ways. The period of time can be any time period, for example, 1 minute or less.

The sensor 80 of the dispenser assembly electronics unit 72 senses the activation signal transmitted by the transceiver 203 and sends a corresponding signal to the controller 78. The controller 78, which is operatively connected to the sensor 80, processes the activation signal using well known methods in the art. In response to the sensor 80 detecting the activation signal, the controller 78 generates a reminder signal. The reminder signal is sent from the controller 78 to one or more of the annunciators 86, 88, 90 to actuate one or more of the annunciators 86, 88, 90 for alarming the user. The alarm, as mentioned above, can be one or more of the light or other visual alarm, the audible alarm, and the tactile alarm, and in some cases two or more of the annunciators can be activated simultaneously or sequentially.

Upon receiving the alarm, the user dispenses the disinfectant fluid, such as by pressing down on the depression button 58 (e.g., bottom surface) of the container 14 to dispense a metered dose of the fluid. Upon the dispensing of the metered dose of fluid the alarm will be terminated. Pressing the depression button 58 actuates an electrical dispensing sensor 89 such as a pressure sensor, flow meter, micro switch, or contact switch 89 that is operatively connected to the controller 78. This dispensing sensor 89 may also be a hall-effect sensor that senses movement of a magnet mounted to the container 14. The dispensing sensor 89 may be located beneath the container 14 in the main housing 12. The dispensing sensor 89 is responsive to dispensing of the fluid, such as by detecting movement of the container 14 or depression of the container 14. Alternatively, the dispensing sensor 89 may be a pressure sensor or flow meter placed in proximity of the nozzle 60 to detect pressure changes or flow caused by movement of the fluid through the nozzle 60. The dispensing sensor 89 sends an electrical signal (dispensing control signal) to the controller 78 indicating that a dispensing event has occurred. The dispensing event is then recorded and saved in the memory, including the date, time, location, etc. of the dispensing event.

Location data can be provided to the controller 78 from the emitter 202. For instance, when deployed, each emitter controller 207 can be programmed with a unique location code or identifier. This code or identifier could be stored in the emitter's memory and transmitted to the controller 78 of the dispenser assembly 10 when the activation signal is transmitted via the interface between transceivers 82, 203.

If the user fails to dispense the fluid after a predetermined period of time has elapsed from the last to be activated alarms (recall that one or more alarms may be sequentially activated), then a "alert—no dispense" event is recorded and saved in the memory, including the date, time, location, etc. of the "alert—no dispense" event. The alarm (or alarms in the case of using multiple alarms) may be terminated after a predetermined period of time even if the user failed to dispense disinfectant fluid. If by the time the alarm is terminated, the user has not dispensed fluid, then a "alert— no dispense" event is recorded and saved in memory for immediate or later transmitting to a monitoring system.

In some embodiments, the controller 78 is configured to delay generation of the reminder signal and thus delay activation of the annunciator 86, 88, 90 (thereby delaying the alarm) in response to the detection of the activation signal for a predetermined period of time. The controller 78 includes a timer to measure the delay (it should be appreciated that the timer may be a function of the controller 78). The delay in the controller 78 sending the reminder signal to the annunciator 86, 88, 90 is measured after the sensor 80 detects the activation signal. The delay is preferably between 1 second and 10 seconds, more preferably between 1 second and 5 seconds, and most preferably between 2 seconds and 3 seconds. This delay provides the user with an opportunity to dispense the disinfectant fluid and avoid the alarm(s) altogether. If the user dispenses the fluid in a manner that is detected by the dispensing sensor 89, a dispensing signal is sent by the dispensing sensor 89 to the controller 78 to disregard the activation signal and bypass the alarm.

If the detected user is not wearing a dispenser assembly 10, a feature can be activated whereby an alarm 205 is activated on the electronic emitter 202. The alarm may be a visual or audible alarm. The transceiver 203 receives an acknowledgement signal back from the transceiver 82 of the electronics unit 72 upon the sensor 80 receiving the activation signal. When no acknowledgement signal is received by the transceiver 203 after a predetermined period of time, usually less than 5 seconds, the emitter controller 207 is programmed to activate the alarm. This indicates that the user does not have a dispenser assembly 10. This is intended to prevent users from entering locations or areas without their dispenser assembly 10 and alerting necessary personnel and the user when such a situation occurs.

The electronic emitter 202 also includes a light source 216. The electronic emitter 202 produces an intermittent beeping noise and flashes the light to indicate that the battery (not shown) of the printed circuit board 212 is low. In response, a new battery can be installed or a new printed circuit board 212 with a new battery may be mounted to the retainer flange 210. The electronic emitter 202 can be powered by category 5 or later version cable, wall power, or battery power, or any other suitable power sources.

In another embodiment, the electronic emitter 202 provides non-overlapping first curtain A and second curtain B to control the particular situations under which the alarm will be initiated. For example, the system 200 could be set such that when a user wearing the dispenser assembly 10 walks into the room and breaks the first curtain A and then the second curtain B, the controller 78 will receive a corresponding signal (e.g., activation signal) to generate the reminder signal.

Conversely, when the user wearing the dispenser assembly 10 exits the room and breaks the second curtain B then the first curtain A, the controller 78 will not generate the reminder signal. This serves to reduce unnecessary alarms that could annoy a user. On the other hand, it is appreciated that certain medical facilities may want the alarm triggered as the user both enters and exits the room to prevent any bacteria obtained during examination from being transmitted outside the examining room. Therefore, the electronic reminder and data collection system 200 includes the option of providing the alarm upon entering the room, or upon entering and exiting the room.

In an alternative embodiment, the electronic emitter 202 includes a wire 218 that is mounted to surround a door, as shown in FIG. 8B. The wire 218 could alternatively be mounted to a bed (not shown). In this embodiment, the wire 218 could surround the bed by being strung along an outer periphery of a base of the bed or within the tubular structure of the bed. The wire 218 acts as an antenna for the electronic emitter 202. More specifically, the wire 218 acts as an antenna for the transceiver 203 of the electronic emitter 202 to transmit a radio frequency (RF) signal to the transceiver 82 of the dispenser assembly 10—similar to an underground pet fence that transmits a radio signal to a receiver on a collar of a pet. The wire 218 may be laid in a closed loop from the transceiver 203 around the door or bed and back to the transceiver 203.

The wire 218 is connected to a power source (which eliminates the need to exchange batteries). The wire 218 may be any number of specified wires. In another embodiment, shown in FIG. 8C, the electronic emitter 202 may be configured for use with a power source 220, such as an electrical discharge aperture, or may be positioned in any of various locations within a room. Thus, when a user wearing the dispenser assembly 10, including the electronics unit 72, enters the room and either comes into range of the activation signal from the electronic emitter 202 (if a continuous activation signal is being transmitted) or is detected by the detector 213 (which in turn triggers the pulsed activation signal), the controller 78 will initiate the alarm which will remind the user, in this case a medical practitioner, to dispense the fluid before interacting with a patient.

The electronic emitter 202 may be mounted in any location. However, in some embodiments, it is preferable to mount the electronic emitter 202 at a location that provides a clear line of sight to the dispenser assemblies 10 (independent of coats, scrubs, or other clothing that may block the line of sight). The electronic emitter 202 may be door jamb mounted, ceiling mounted, wall mounted, surface-mounted, or bed mounted. In some cases the electronic emitter 202 has a mount in the form of a clip (not shown) that is releasably mounted to a separate fixed base (not shown) on the door jamb, wall, or bed. In other cases, the electronic emitter 202 includes a mount in the form of a magnet (not shown) fixed to the backing member 208 thereof for releasable attachment to certain metal surfaces. The electronic emitter 202 may include mounts of any type or configuration such as a simple bracket (not shown) or base (not shown). In other embodiments, the electronic emitter 202 may simply have a mount in the form of a movable stand similar to a picture frame table stand.

In another alternative embodiment, the controller 78 can be programmed to activate the alarm for certain intervals, dates, or times. For example, the controller 78 can be programmed to activate the alarm to go off just before the lunch hour to remind school children to dispense a particular fluid, such as a disinfectant. In another example, the controller 78 can be programmed to activate the alarm to go off just before a scheduled surgery to remind a medical practitioner to dispense the particular fluid. To ensure use of the dispenser assembly 10, the alarm is terminated when the metered dose of fluid is dispensed by the dispenser assembly 10 and detected by the dispensing sensor 89. In some embodiments, the alarm is terminated when the dispensing event is detected by the dispensing sensor 89, independent of whether a full metered dose of fluid is dispensed, such as when the container 14 only contains a portion of a dose.

As mentioned above, the dispenser assembly 10 may also be configured to generate the warning alert to notify the user when the fluid level in the container 14 is low. The warning alert could be a light (or other visual alarm), an audible alarm, or a vibration that is different from the alarm. The counter counts dispensing events based on actuation of the dispensing sensor 89. The counter is an operative part of the controller 78. The controller 78 monitors the number of dispensing events by counting the number of separate signals received from the dispensing sensor 89. The controller 78 alerts the user when the container 14 has low fluid based on a predetermined estimate of the number of dispensing events contained in the container 14. The controller 78 also resets the counter to zero upon receiving a new container 14.

In other embodiments a weight sensor (not shown) is mounted to the main housing 12 to determine the weight of fluid remaining in the container 14. This prevents a user from fake dispensing an empty container 14 and also provides another method of determining the amount of fluid remaining in the container 14. The user may also be required to press the button 87 to send a signal to the controller 78 that a new container 14 has been placed in the dispenser assembly 10 to reset the counter to zero and prevent inadvertent resetting of the counter to zero when the container 14 is inadvertently pulled from the dispenser assembly 10 but then immediately replaced.

In still another embodiment, the dispenser assembly 10 functions as a locating device. The dispenser assembly 10 may include a GPS location device 94 for determining location information associated with the dispenser assembly 10. The GPS location device 94 includes a GPS antenna and periodically performs a GPS routine to determine the longitude and latitude of the dispenser assembly 10. The GPS location device 94 is connected to the controller 78. The controller 78 retrieves the location information from the GPS location device 94 and stores the location information in the memory 84. The dispenser assembly 10 continuously or periodically transmits the location data to a monitoring system 300 using the transceiver 82 via a radio link or other type of wireless link.

Figure 8D:
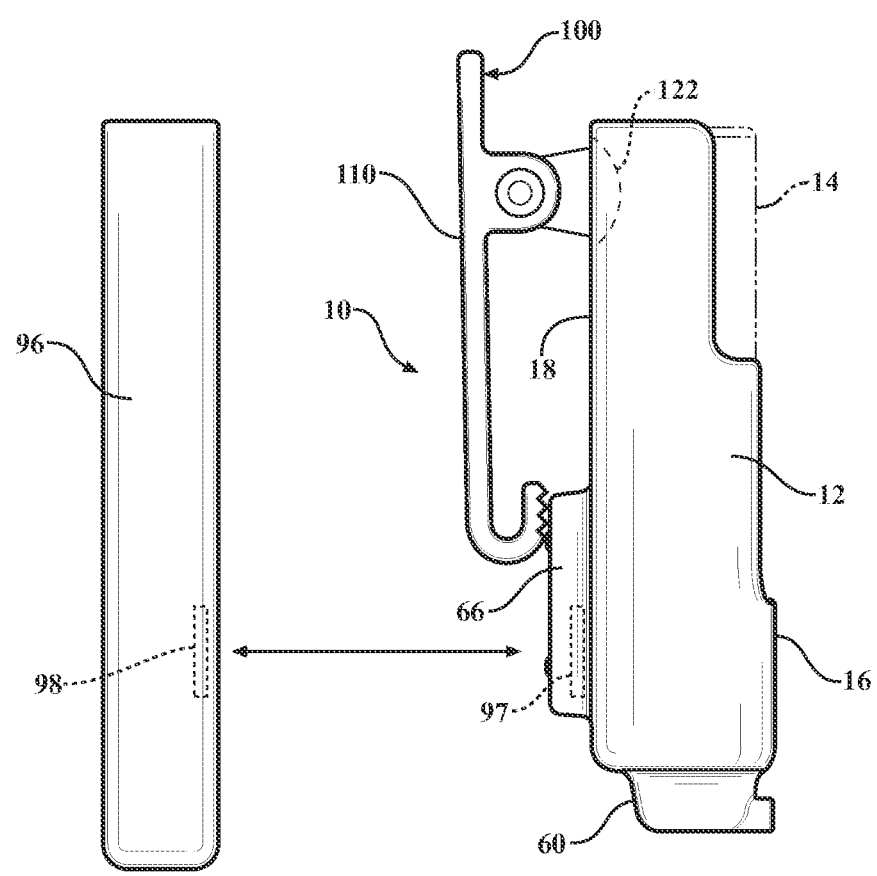
FIG. 8D is an illustration of the dispenser assembly communicating with a personal digital assistant (PDA)

Referring to FIG. 8D, in one embodiment, the dispenser assembly 10 is configured to interface with a nearby handheld electronic device 96. The handheld electronic device 96 can be a personal digital assistant (PDA), smart phone (such as an iPhone® model of smart phone made by Apple Inc.) or other handheld electronic device. The handheld electronic device 96 may be held by the user or another person.

The dispenser assembly 10 has a first transceiver 97 capable of short range wireless communication, such as communication employing Bluetooth protocol, or other forms of wireless communication. The first transceiver 97 is operatively connected to the controller 78 of the electronics unit 72. A second transceiver 98 is located on the handheld electronic device 96. The second transceiver is also capable of short range wireless communication, such as communication employing Bluetooth protocol, or other forms of wireless communication. The second transceiver 98 may be located on a motherboard (not shown) of the handheld electronic device 96 in communication with a device controller having a data processor (not shown). Such transceivers include those employed on the iPhone® models of smart phone. The first transceiver 97 is capable of communicating with the second transceiver 98 through a communication channel. In other embodiments, the dispenser assembly 10 and the handheld electronic device 96 may include any suitable components for facilitating short range communication with each other, such as a transmitter, a receiver, and the like.

Through the communication channel between the handheld electronic device 96 and the electronics unit 72, data can be transmitted from the handheld electronic device 96 to the electronics unit 72 or vice versa. For instance, the handheld electronic device 96 may have device data such as GPS location data to transmit to the electronics unit 72 through the communication channel. The device data may be stored in the memory on the handheld electronic device 96 during use for later transmitting to the electronics unit 72 when prompted. The device data may be transmitted from the second transceiver 98 of the handheld electronic device 96 to the first transceiver 97 of the dispenser assembly 10 when the dispenser assembly 10 initiates connection between the transceivers 97, 98 and/or anytime the controller 78 sends a data transfer request signal to the device controller through the communications channel.

Alternatively, the electronics unit 72 has dispensing event data relating to the dispensing events that could be transmitted to the handheld electronic device 96 through the communication channel. The dispensing event data may be stored in the memory 84 of the electronics unit 72 during use for later transmitting to the handheld electronic device 96 when prompted. The dispensing event data may be tagged with the unique identifier associated with the dispenser assembly 10 that is stored in the memory 84. The dispensing event data may include dates and times of dispensing events or, in some cases, dates and times of "no-dispense" alerts. The dispensing event data may be transmitted from the first transceiver 97 of the dispenser assembly 10 to the second transceiver 98 of the handheld electronic device 96 when the handheld electronic device 96 initiates connection between the transceivers 97, 98 and/or anytime the device controller sends a data transfer request signal to the controller 78 through the communications channel.

Once the device data and the dispensing event data are located (e.g., stored) on a single device, either the handheld electronic device 96 or the dispenser assembly 10, the device data can be correlated to the dispensing event data for later sending to a monitoring system 300, as described below, for monitoring hand hygiene of the user.

In one version, the dispenser assembly 10 may be assigned to a home health care professional charged with attending to multiple patients located at different residential addresses. In this instance, the handheld electronic device 96 may be a smart phone, such as an iPhone® model of smart phone assigned to the home health care professional. The home health care professional uses the dispenser assembly 10 to maintain hand hygiene while attending to each of the patients at the different residential addresses. During this use, the dispenser assembly 10 is recording the dates/times of each dispensing event, i.e., each date/time the home health care professional dispenses fluid from the dispenser assembly 10 is saved in the memory 84. Simultaneously, the handheld electronic device 96 carried by the home health care professional is recording location data associated with the location of the handheld electronic device 96. By virtue of the home health care professional carrying both the dispenser assembly 10 and the handheld electronic device 96 to each residential address, the dates/times of the dispensing events can be correlated to the location data. This correlated data, e.g., the dispensing event data correlated to the device data, can then be transmitted to the monitoring system 300 thereby providing the monitoring system 300 with information regarding the location of the dispensing events. For instance, the information may include, for a given time period, the dispensing events that occurred, and the residential address at which each dispensing event occurred.

A software application may be used to transfer the dispensing event data from the dispenser assembly 10 to the handheld electronic device 96, correlate the dispensing event data with the device data, and transfer the correlated data to the monitoring system 300. The software application is installed on the handheld electronic device 96 and uses native controls of the handheld electronic device 96. The data processor of the handheld electronic device 96 executes code/instructions stored in its memory for implementing the software application. When the handheld electronic device 96 is an iPhone® model of smart phone, the software application is an iOS application, which is a computer program that operates on the iOS operating system provided by Apple Inc. The iOS application provides an icon on a display of the handheld electronic device 96 for ease of access by the user, similar to other known iOS applications ("apps").

A database is also stored in the memory of the handheld electronic device 96 to be accessed by the iOS application. In one embodiment, upon accessing the iOS application on the handheld electronic device 96 (colloquially referred to as opening the app), the iOS application initiates a transfer of dispensing event data from the memory 84 of the electronics unit 72, through the communication channel, to the database. The handheld electronic device 96 may then correlate the device data, such as the location data previously stored in the memory of the handheld electronic device 96, with the dispensing event data as previously described. For instance, the database may include the dates/times of the dispensing events, the dates/times of "no-dispense" alerts, and the locations of each dispensing event or "no-dispense" alerts. This provides a record of when/where dispensing events occurred. The correlated data in the database can then be transmitted via a separate wired or wireless connection to the monitoring system 300 from the handheld electronic device 96.

In other versions, additional electronic capabilities of the handheld electronic device 96 may be utilized with the dispenser assembly 10 such as the alarm, photo/video capabilities, etc. For instance, the alarm functionality on the iPhone® models of smart phone may be used to prompt the dispensing events of the user. The alarm could be set up by the iOS application to occur at predetermined times to prompt the user to dispense fluid. Similarly, the electronics unit 72 of the dispenser assembly 10 could be configured to transmit a dispensing signal to the handheld electronic device 96 to indicate that a dispensing event has occurred to turn off the alarm or prevent the occurrence of the alarm.

The electronics unit 72 and/or the emitter 202 may be configured with a sleep mode to conserve battery power. For instance, the controller 78 may shut down the display 86 of the dispenser assembly 10 after a predetermined period of non-use. Further, the electronic emitter 202 may use the detector 213 to activate the electronic emitter 202 from the sleep mode. When motion is not detected, the electronic emitter 202 is in the sleep mode, but when the detector 213 detects the user, the electronic emitter 202 is activated to transmit the activation signal to the dispenser assembly 10.

Figure 8E:
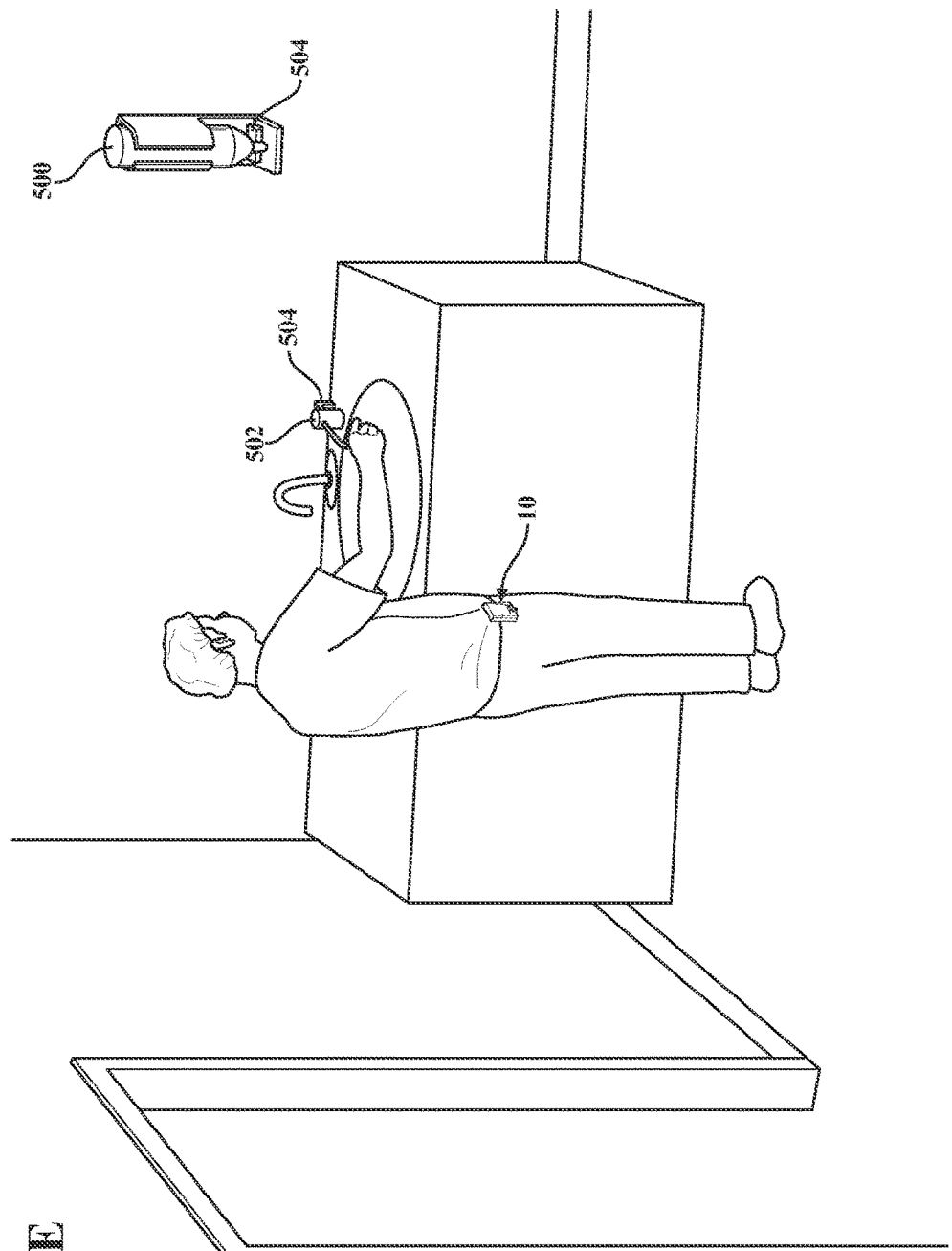
FIG. 8E is an illustration of wall-mounted and sink-mounted dispensers with detection units.
Figure 11:
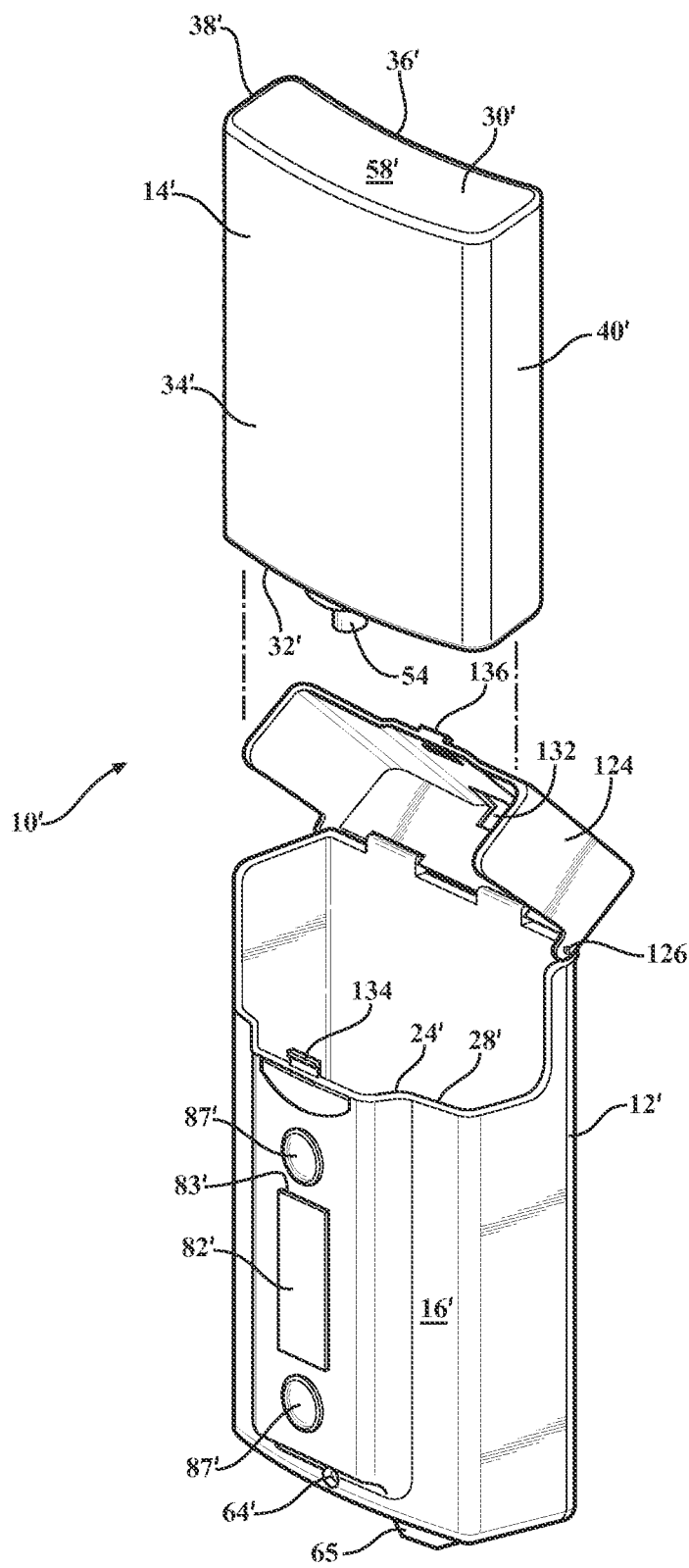
FIG. 11 is an exploded perspective view of the dispenser assembly in a second embodiment of the invention.
Figure 14:
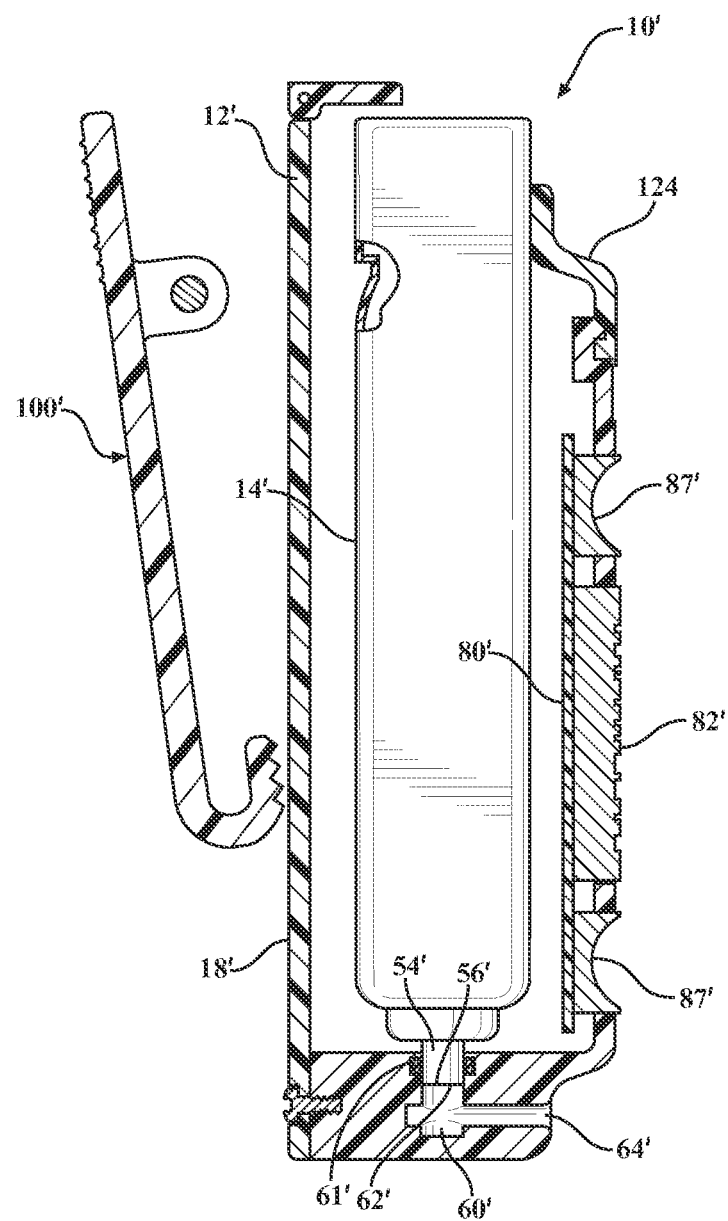
FIG. 14 is a cross-sectional view of the dispenser assembly taken along lines 14-14 in FIG. 9.

Referring to FIG. 8E, the hospital or other facility in which the dispenser assemblies 10 are utilized may also have wall-mounted dispensers 500 and/or sink-mounted dispensers 502 to dispense disinfectant (e.g., sanitizer or soap). It should be appreciated that the sink-mounted dispenser 502 could be a soap dispenser that is also mounted on the wall. Should the user decide to use the wall-mounted dispensers 500 or the sink-mounted dispensers 502 instead of the dispenser assembly 10, then a signal is sent to the dispenser assembly 10 indicating a dispensing event has occurred and either preventing the alarm or satisfying the alarm and thereby shutting off the alert. The alert may also be deactivated for a predetermined period of time such as 30 seconds or less. This accounts for situations in which the user receives the fluid from a wall-mounted dispenser 500 outside of the room and then enters the room. By disabling the alert for the predetermined period of time, the user is not annoyed with an alert after having just recently sanitized their hands. After expiration of the predetermined period of time, the dispenser assembly 10 would reset allowing further alerts.

The wall-mounted 500 and sink-mounted 502 dispensers are retrofitted (or may be original equipment) with detection units 504. The detection units 504 include an electric switch (not shown) that is actuated upon dispensing of disinfectant from the wall-mounted 500 and sink-mounted 502 dispensers. The electric switch may be electrically actuated such as by a motion sensor, hall-effect sensor, or may be mechanically actuated such as by a lever or other mechanical switch attached to the dispenser 500, 502 that moves when the dispenser 500, 502 is operated. The electric switch communicates with a controller (not shown) of the detection unit 504. The controller may be the same make and model as controller 78. The detection units 504 also include a transceiver (not shown) in communication with the detection unit controller that transmits a dispensing signal indicating a dispensing event has occurred when instructed by the detection unit controller.

The dispensing signal may be any variety of wireless signals including infrared, RF, and the like. The dispensing signal is received by the sensor 80 (e.g., antenna of transceiver 82) on the dispenser assembly 10. The dispenser assembly electronics unit transceiver 82 transmits an acknowledgement signal back to the transceiver on the detection unit 504 upon receipt of the dispensing signal. The detection unit controller then terminates the dispensing signal so that other dispenser assemblies 10 are not inadvertently credited with the dispensing event.

The dispenser assembly 10 may also be configured to account for multiple sequential dispensing events that could occur when a user actuates the wall-mounted 500 and sink-mounted 502 dispensers multiple times such as by pulling the lever twice to dispense additional material. In this case, the controller 78 may be configured to lump multiple dispensing events that occur within a predetermined time period as being one event for tracking purposes. For instance, all dispensing events that occur within 2 seconds of each other could be considered one dispensing event.

In FIG. 8E, the user has actuated the sink-mounted dispenser 502, which generates a control signal from the electric switch of the detection unit that is sent to the detection unit controller. As a result, a dispensing signal is transmitted from the transceiver of the detection unit 504 for receipt by the transceiver 82 of the dispenser assembly 10. When the dispensing signal is received by the transceiver 82, the controller 78 instructs the transceiver 82 to then send the acknowledgement signal back to the transceiver of the detection unit 504. The transceiver of the detection unit 504 could be the same as the transceivers 82, 203 (including antenna).

The controller 78 also stores data related to this dispensing event in the memory 84. The data may include the date/time of the dispensing event per the clock 92, the location of the dispensing event per GPS or programmed data stored in a memory of the detection unit 504 similar to location data stored in the emitter 202, a unique identifier associated with the sink-mounted dispenser 502, and the like.

It is further appreciated that the specific functions of the dispenser assembly 10 will vary depending on the user. For example, the dispenser assembly 10 may include a locator and alarm for use by children, while the dispenser assembly 10 for medical use would include infrared/Bluetooth/hard wired reminders for medical practitioners and also become a disinfectant carrier with a beeper incorporated into the carrier so that medical practitioners will avoid having to wear two devices. These function options could be selected on the electrical panel by special programming and/or the use of dip switches to turn on the options specifically required for the particular unit.

Referring back to FIGS. 3 through 6, the dispenser assembly 10 includes a mounting element such as a lanyard (not shown) or a clip assembly coupled to the main housing. The mounting element, allows for attachment of the dispenser assembly 10 to a user's waist belt, lapel, pocket, stethoscope, or the like. In the embodiment shown, the mounting element is a clip assembly, generally indicated at 100, to allow for attachment of the dispenser assembly 10 to a user's waist belt, pocket or the like. The clip assembly 100 includes mounting arms 102, 104 extending out from the outboard surface 67 of the back wall 18. A post 108 extends through the mounting arms 102, 104. A clip 110 rotates about the post 108 to move the clip assembly 100 between a closed position, shown in FIG. 5, and an open position. The clip 110 includes an upper end 112 and a lower end 114. The lower end 114 in one embodiment is generally U-shaped. A biasing member 116 is secured to the post 108 for biasing the clip assembly 110 towards the closed position. The biasing member 116 includes ends that abut the back wall 18 and the clip 110 respectively.

In one embodiment, the main housing 12 along with the container 14 secured thereto may rotate relative to the clip assembly 100 about a base portion 122, as shown in FIG. 5. Thus, a user wearing the dispenser assembly 10 in the standard upright vertical position, i.e., with the depression button 58 forming the uppermost surface of the container 14, may rotate the main housing 12 and container 14 relative to the clip assembly 100 approximately 45 to 90 degrees up to a generally horizontal position such that the depression button 58 is now located along one side of the dispenser assembly 10. As a result, the depression button 58 is less susceptible to contact from a user's stomach, thereby reducing the possibility of accidental dispensing of fluid. It is further appreciated that the user could rotate the main housing 12 and container 14 to any of numerous use positions from the standard upright vertical position. The base portion 122 may include a click or detent mechanism that clicks into place to let the user know that the main housing 12 and container 14 are in one of various predetermined positions.

Referring to FIGS. 9 through 14, wherein like primed reference numerals represent similar elements as those set forth above, the dispenser assembly 10' in a second embodiment of the invention includes the main housing 12' and a lid 124 pivotally secured thereto about a hinge 126. It is appreciated that the particular size and shape of the main housing 12' may vary. The lid 124 includes a top surface 128 and a front surface 130. The lid 124 defines a window opening 132 extending through a portion of the top 128 and front 130 surfaces. The lid 124 also includes a coupling portion (not separately numbered) which is engageable with a locking tab 134 formed along the upper edge 24' of the front wall 16' of the main housing 12' in order to maintain the lid 124 in a closed position, shown in FIGS. 9 and 10. The lid 124 further includes a release tab 136 that can be pulled to move the lid 124 from the closed position to an open position, shown in FIG. 11.

The container 14' is filled with fluid as described above and is removably disposed within the cavity 28' of the main housing 12'. When the lid 124 is closed, the container 14' is securely held inside the cavity 28'. And when the lid 124 is opened, the container 14' may be removed and replaced with a new container 14'. In one embodiment, the container 14' is a pressurized canister that is well-known to those of ordinary skill in the art. The container 14' includes the stem 54' with the open end 56'. The stem 54' is in fluid communication with the nozzle 60', which is integrally formed with the main housing 12'. The nozzle 60' includes the fluid discharge aperture 64'. When the user presses downwardly on the depression button 58', a continuous amount or predetermined amount of the fluid within the container 14' will be expelled out of the fluid discharge aperture 64'.

The window opening 132 of the lid 124 allows users to access the underlying depression button 58'. The positioning of the depression button 58' underneath the window opening 132 prevents users from accidentally dispensing fluid from the dispenser assembly 10'. More specifically, a user must place their finger through the window opening 132 to press the depression button 58' and dispense the disinfectant. The lid 124 covers the corners of the container 14' while defining the window opening 132 that exposes the depression button 58'. By covering the corners of the container 14', it is more difficult for the user to inadvertently press the depression button 58' with their stomach, elbow, and the like. In another embodiment, a spring (not shown) is associated with the nozzle 60' and is disposed between the container and nozzle 60' such that a greater amount of pressure is required to press the depression button 58' and activate the dispenser assembly 10'. This embodiment eliminates the problem of inadvertently operating the dispenser assembly 10' via only the application of mild pressure. The spring would also increase the bias against the container 14' to lift the container 14' and return the container 14' to its normal position for subsequent use.

In an alternative embodiment, the container 14' may include a convex protrusion or button-like protrusion formed in a concave bottom portion that is pushed to dispense the fluid. This prevents inadvertent operation of the dispenser assembly 10' by positioning the activation mechanism at the bottom of the dispenser assembly 10'. The button on the lid 124 may be embossed or inset so that it will not be accidentally pushed. In another embodiment, the dispenser assembly 10' has a flat bottom cover over a concave container 14' to have an object to push. The concave shape would move the surface of the container 14' further from the surface of the main housing 12', thus making it difficult to push the container 14'. In yet another embodiment, a tab is positioned at the top of the main housing 12' to assist in pushing the container 14'.

It is contemplated that the container 14' may include a honeycomb center, a multi-layer laminate, or an internal bladder to withstand any pressure required to maintain the shape of the container 14'. In an alternative the container 14' may include a refill port such that the container 14' can be refilled with fluid using a higher pressurized container.

The main housing 12 includes at least one flange to provide an interference fit of the container 14'. In one embodiment, the flange is formed from a soft material and/or liner, such as mole skin or flocking material, to prevent scratching of the container 14'. In one embodiment, the inner walls of the main housing 12' may be coated in a soft material or liner in order to prevent the main housing 12' from scratching the container 14'.

Figure 15:
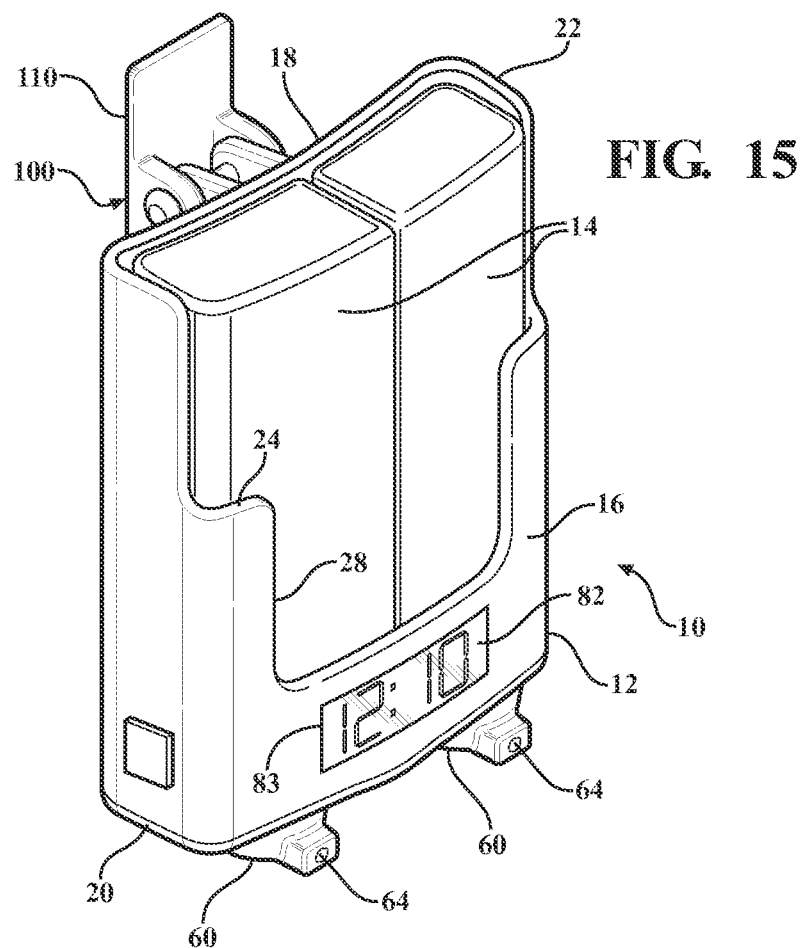
FIG. 15 is a perspective view of a dispenser assembly according to a third embodiment of the invention.

Referring to FIG. 15, in certain embodiments, multiple containers 14 are loaded in the dispenser assembly 10. Each container 14 may hold the same type of fluid or different fluids. In some embodiments, a first fluid may contain a conventional disinfectant designed to kill some bacteria and a second fluid may contain a disinfectant designed to kill other types of bacteria that cannot be killed by the disinfectant in the first fluid. The fluids of the separate containers 14 may also be simultaneously dispensed and intended to act together to disinfect the user. In this embodiment, the components previously described for each canister 14 are doubled, including the nozzle 60 and discharge aperture 64. Also, separate dispensing sensors 89 are included to communicate with the common controller 78 to indicate when each of the containers 14 have been dispensed. In some embodiments, the alarm, once activated, will continue to sound until both containers 14 have been dispensed. Dispensing event data may also be kept separately for each container 14. In other embodiments, two or more containers can be actuated to mix their contents into a single nozzle during dispensing (not shown).

Figure 16:
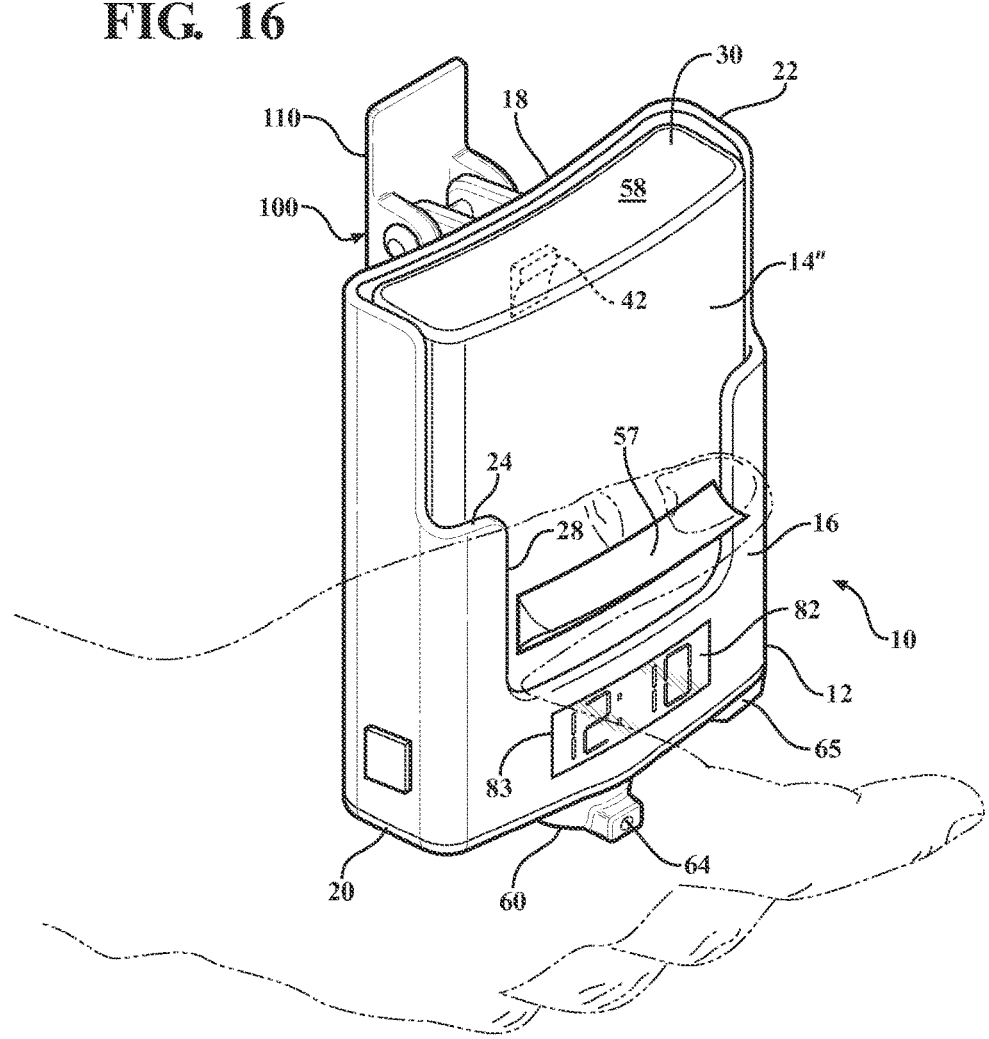
FIG. 16 is a perspective view of a dispenser assembly according to a fourth embodiment of the invention.

Referring to FIG. 16, the container 14" in yet other embodiments may include a lever 57. The lever 57 is located lower than the button 58 for easier access by a user. The main housing 12 includes a vertical slot through which the lever 57 protrudes. The lever 57 provides better leverage for dispensing for certain users with smaller hands. In this embodiment, the user squeezes the lever 57 while simultaneously holding the bottom of the dispenser assembly 10 as shown. The lever 57 provides an advantage for users with small hands that may not be able to reach the top of the container 14" and the bottom of the dispenser assembly 10 simultaneously, thereby making it difficult to dispense the fluid.

Figure 17:
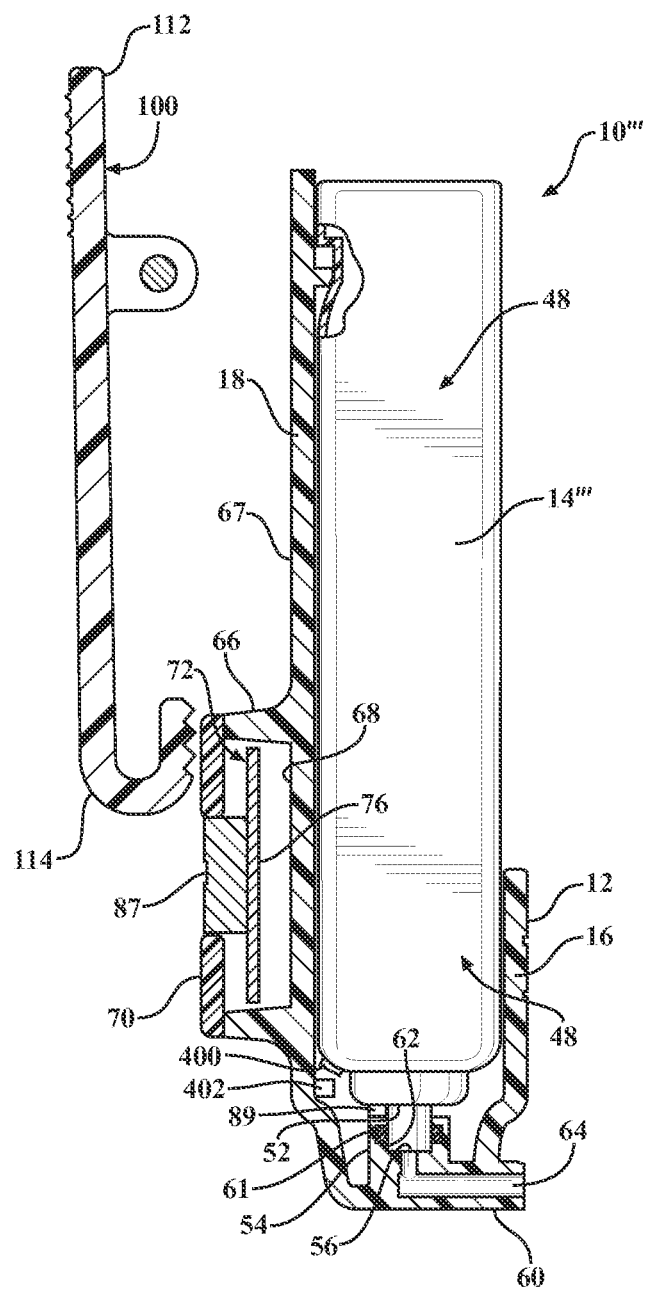
FIG. 17 is a cross-sectional view showing a container with RFID tag and the dispenser assembly with an RFID reader.

Referring to FIG. 17, each container 14''' may have a RFID tag 400 or similar identification tag mounted to the container 14''', such as on a side or bottom of the container 14'''. The dispenser assembly 10''', in this embodiment, is equipped with a RFID reader 402 for reading the RFID tag 400 when the container 14''' is placed in the housing 12. The RFID reader 402 is in electrical communication with the controller 78. The RFID reader 402 sends identification data to the controller 78 when reading the RFID tag 400. The RFID tag 400 and RFID reader 402 are aligned, or at least in close proximity to one another, when the container 14''' is placed in the main housing 12. The RFID tag 400 has a unique identifier for each container 14''' to prevent the reuse of the same container 14''' and to ensure use with manufacturer specified containers. For instance, when the container 14''' is empty and the user is required to replace the empty container with a new full container 14''', the user is prevented from merely placing the same empty container 14''' or another previously used container into the dispenser assembly 10''' since the memory 84 of the dispenser assembly 10 stores the unique identifiers of all prior used containers and the controller 78 compares those to the new container unique identifier. If the container being used is a prior, already used and empty container, then the electronics unit 72 sends an alert, e.g., alarm, via the controller 78 and one or more annunciators for a period of time or until a new container 14''' is used. That event will also be recorded into the system similar to a dispensing event. If a new canister is not placed, the controller 78 will shut down and log the event and alert the administrator of the error through the communication methods described herein. Additionally, the container unique identifiers may include a manufacturer specific code that prevents use of other non-specified containers. In this case, the controller 78 would evaluate the RFID tag 400 to determine whether the manufacturer specific code is present and if not, disables the system and alerts the administrator.

In some embodiments, each container 14 may have a portion (e.g., dot) painted with ferrite paint or other identifying substance that can be electronically detected. The dot may be located on the container 14 as part of indicia such as lettering on the container 14. The paint may be located in the same position on each container 14 so that a detector (e.g., a hall-effect sensor), which communicates with the controller 78, can detect the container 14. In these embodiments, the paint would be located in a small spot on the outer surface of the container, preferably less than one inch in diameter, and more preferably less than one quarter inch in diameter. The detector can detect the paint when the paint is positioned in opposing proximity to the detector. For instance, if the paint is located on the bottom of the container 14, then the detector would be located on the bottom wall 26 of the main housing 12 such that when the container 14 is inserted into the main housing 12, the paint is longitudinally aligned with the detector. The detector would then transmit a signal to the controller 78, to indicate that a container 14 with the appropriately located paint spot has been placed in the main housing 12. If a container without the paint spot is loaded into the dispenser assembly 10, then the controller 78 would trigger the alarm through the devices previously described. After the alarm is triggered, if a proper container is not placed into the dispenser assembly 10, the event will be recorded into the system similar to a dispensing event indicating the occurrence and error and then the dispenser assembly 10 will not properly function. In other words, the controller 78 will shut down and log the event and alert the administrator of the error through the communication methods described herein.

Figure 17A:
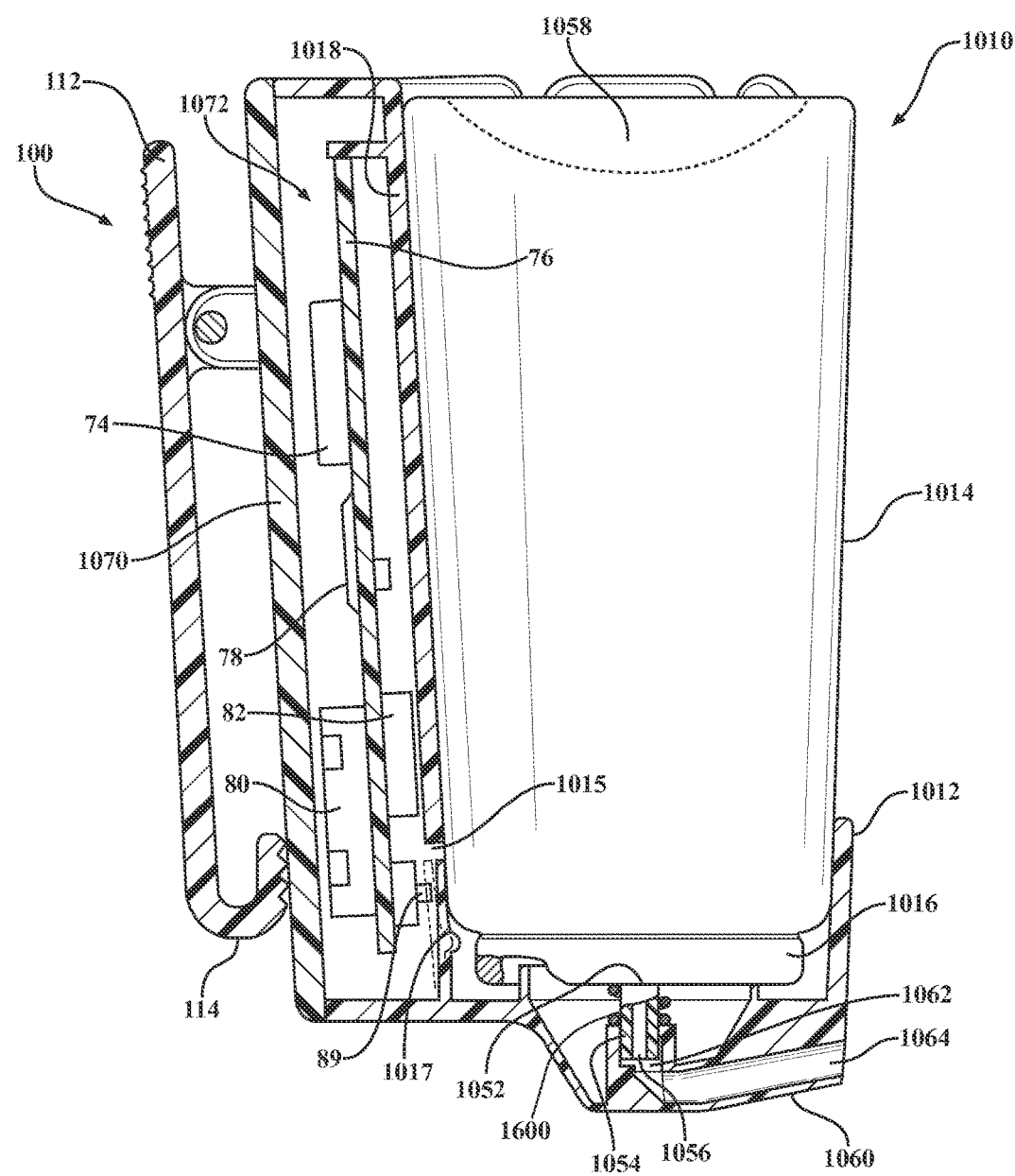
FIG. 17A is a cross-sectional view of another embodiment of the dispenser assembly.

Referring to FIG. 17A, another embodiment of dispenser assembly 1010 is shown. In this embodiment, the numerals have been increased by 1000 to show similar parts relative to the embodiment of FIG. 6. In this embodiment, the dispensing sensor 89 is a mechanical micro switch that is actuated by depressing a flexible portion 1017 of the back wall 1018 with the container 1014 when dispensing the fluid. The flexible portion 1017 may be a tab that pivots in an opening 1015 in the back wall 1018. The flexible portion 1017 has a camming surface (not separately numbered) that is engaged by the container 1014 and configured to flex when the container 1014 is depressed. When flexed, as shown by hidden lines, the flexible portion 1017 is pushed to the left to contact and depress the dispensing sensor 89. Upon being depressed, the dispensing sensor 89 transmits a signal to the controller 78 that a dispensing event has occurred. It is to be appreciated that other methods may be used to signal a dispensing event to the controller 78.

FIG. 17A also illustrates a biasing device 1600 disposed about the stem 1054. In the embodiment shown the biasing device 1600 is a spring 1600 that urges the container 1014 upwardly into an initial state in preparation for actuation by the user. The spring 1600 is compressed when the user presses the container 1014 downwardly by depressing button 1058. After the button 1058 is depressed so that the pump mechanism 1052 dispenses a full dose of disinfectant, the spring 1600 acts to lift the container 1014 back to the initial state. In other embodiments the biasing device 1600 may be compliant foam pads or other devices suitable for biasing the container 1014. It should be appreciated that the pump mechanism 1052, whether from an aerosol container or other type of container, also has a biasing feature such as a spring that is capable of urging the container 1014 into the initial state. Such biasing devices are conventional in the dispensing container arts and are thus not described in detail. In such a case, the biasing device 1600 acts as a secondary biasing device to ensure that the container 1014 returns to the initial state.

Referring to FIG. 7, the electronic data collection and reminder alert system 200 includes the electronics unit 72. The electronics unit 72 stores in its memory 84 data relating to the user and the user's dispensing events, e.g., date, time, use location, and any of a variety of additional data. Each dispenser assembly 10 is assigned a unique identifier or code (e.g., dispenser digital ID) that corresponds to an individual, and the data is associated with the unique code and can be provided to a participating hospital, corporation, or other entity or facility.

The electronic reminder and data collection system 200 is configured to transmit the data, including date, time, and location of dispensing events, along with the associated unique code, to the monitoring system 300. The monitoring system 300 is configured to operatively connect to the electronics unit 72 of the dispenser assembly 10 in one of a wired or wireless connection to receive the data associated with the dispensing events. In some embodiments, the transceiver 82 on the dispenser assembly 10 includes a wireless transmitter (e.g., the ground planar antenna) for wirelessly transmitting the dispensing event data along with the unique identifier to a wireless transceiver 301 of the monitoring system 300. Communication between the electronics unit 72 of the dispenser assembly 10 and the monitoring system 300 is shown by a double arrow in FIG. 7.

The monitoring system includes a computer 303 in wired or wireless communication with the dispenser assemblies 10 via the transceivers 82, 301 or other interface to transfer the dispensing event data along with the unique identifier. The transceiver 301 may be the same make and model as the transceivers 82, 203. The computer 303 may be a server, a personal computer, a laptop computer, or the like, any of which may operate as a server. The computer 303 includes at least one central processing unit (CPU) or processor for processing the data, memory, storage, input and output devices such as a mouse, keyboard, display, and printer. The computer 303 includes a database (not separately numbered) for storing the data for later retrieval, review, and/or reporting. In some embodiments, the data is stored in a spreadsheet application (e.g., Microsoft Excel) for later retrieval, review, and/or reporting.

In some embodiments, the data from the dispenser assemblies 10 is first transmitted, either wired or wirelessly, to a base station (e.g., controller with wired or wireless transceiver)(not shown) that receives the data electronically from the transceiver 82 and converts the data into a format readable by the software within the computer 303. In this embodiment, the base station includes a housing (not shown). A printed circuit board (not shown) is supported by the housing. The controller for the base station (not shown) is located on the printed circuit board and can be the same make and model of controller as controller 78. In this embodiment, the transceiver 301 is also located on the printed circuit board in communication with the base station controller and could be the same make and model of transceiver as transceivers 82, 203. The computer 303 is in wired or wireless communication with the base station through the transceiver 301 to receive the data electronically, after conversion, from the base station.

The monitoring system 300 may further be in communication with a cloud computer, cloud server, and/or cloud data storage system (shown as "cloud" in FIG. 7) and in some embodiments, the data from the dispenser assemblies, or from the handheld electronic device 96, is first transmitted to the cloud. The computer 303 can then access the data from the cloud.

The monitoring system 300 may be in wired or wireless communication with the electronic emitters 202 via the computer 303 so that the monitoring system 300 can further monitor, program, or otherwise be integrated with the electronic emitters 202. In this embodiment, the dispensing data saved in the dispenser assemblies 10 could be transmitted first to the electronic emitter 202 and then to the computer 303. In other words, in some embodiments, the emitter 202 acts as the base station that first receives the data electronically from the transceiver 82, converts the data into a format readable by the software within the computer 303 and then transmits, either wired or wirelessly, the data to the computer 303.

The computer 303 runs a computer program 302 that converts the received data into a readable format for display or reporting. The reports detail the date, time, location of dispensing events, and additional information of the dispenser assembly 10 for the individual identified by the unique identifying code. The reports and/or data can be transferred to a computer network 304 through a wired or internet connection such as Ethernet connection and accessed by a personal computer 306 or PDA. Thus, the electronic data collection and reminder alert system 200 and monitoring system 300 allows an organization to collect valuable data that can be used to measure frequency of hand hygiene, hand hygiene events, rate of hand hygiene compliance and the effectiveness of the entire system including the alarms provided by the dispenser assembly 10, and the monitoring system and substantiate the use of the dispenser assemblies 10, and improve upon the program for future applications.

Referring to FIGS. 18-22, screen shots of the software 302 used on the computer 303 of the system is illustrated. The software 302 was created in the LabVIEW graphical programming environment. The software 302 could similarly be created using other programs. In some cases, the computer 303 receives the data upon a "handshake" between the transceiver 82 of the dispenser assembly 10 and a wired or wireless communication device (e.g., transceiver 301, router, wireless adapter, etc.) connected to the computer 303. Once the transceiver 82 and the wired or wireless communication device establish the communication channel and corresponding parameters for communication, the data is transferred from the dispenser assembly 10, such as from the memory 84, to the computer 303 of the monitoring system 300.

Figure 18:
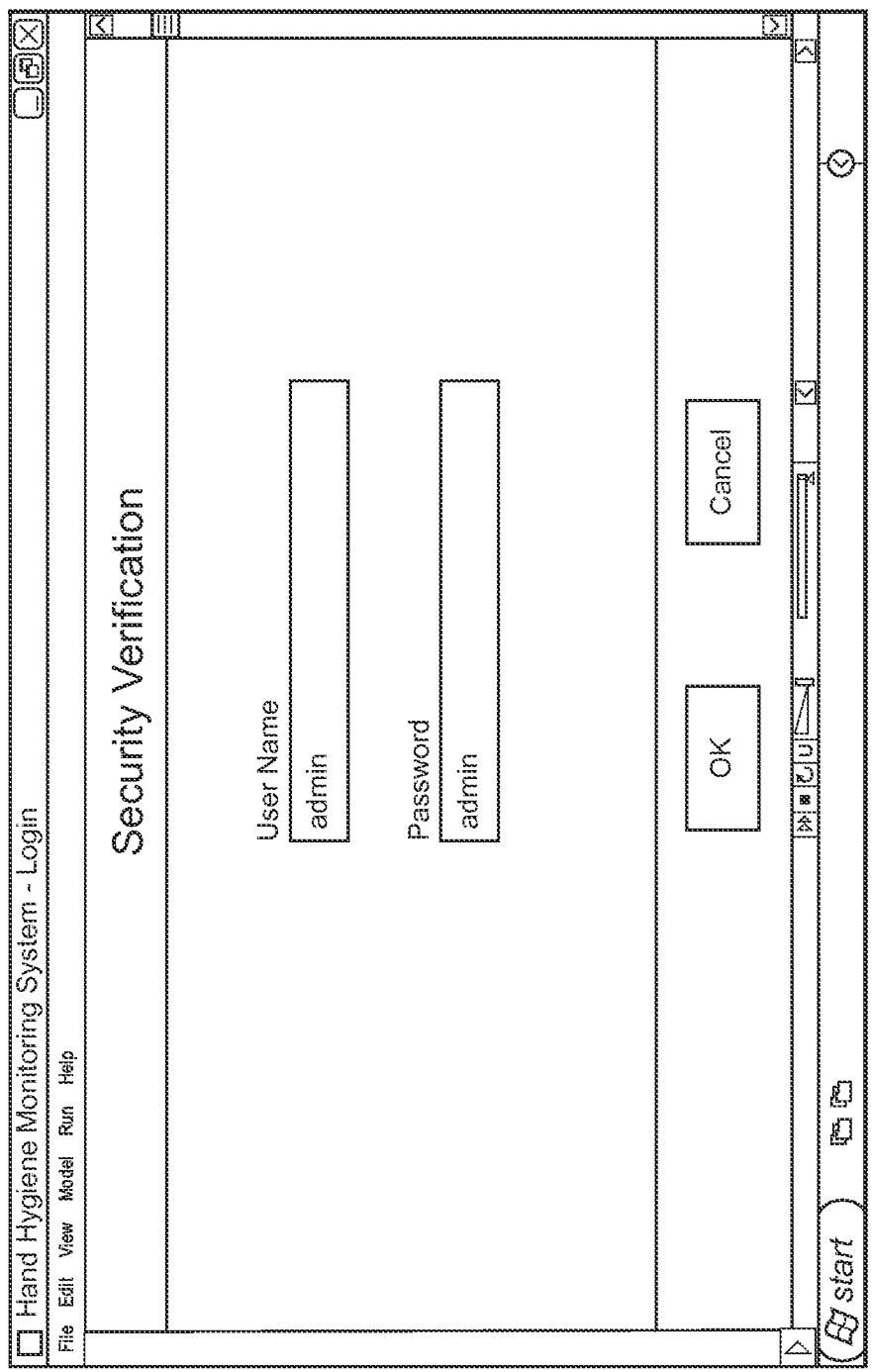

FIG. 18 illustrates a login screen of the software 302. As is conventional in most software applications, the login screen requires entry by a user of a User Name and Password. Once the appropriate User Name and Password is recognized by the computer 303, the main monitoring interface of the software 302 is displayed on the display of the computer 303. The main monitoring interface shows the tracking of multiple dispenser assemblies 10.

Figure 19:
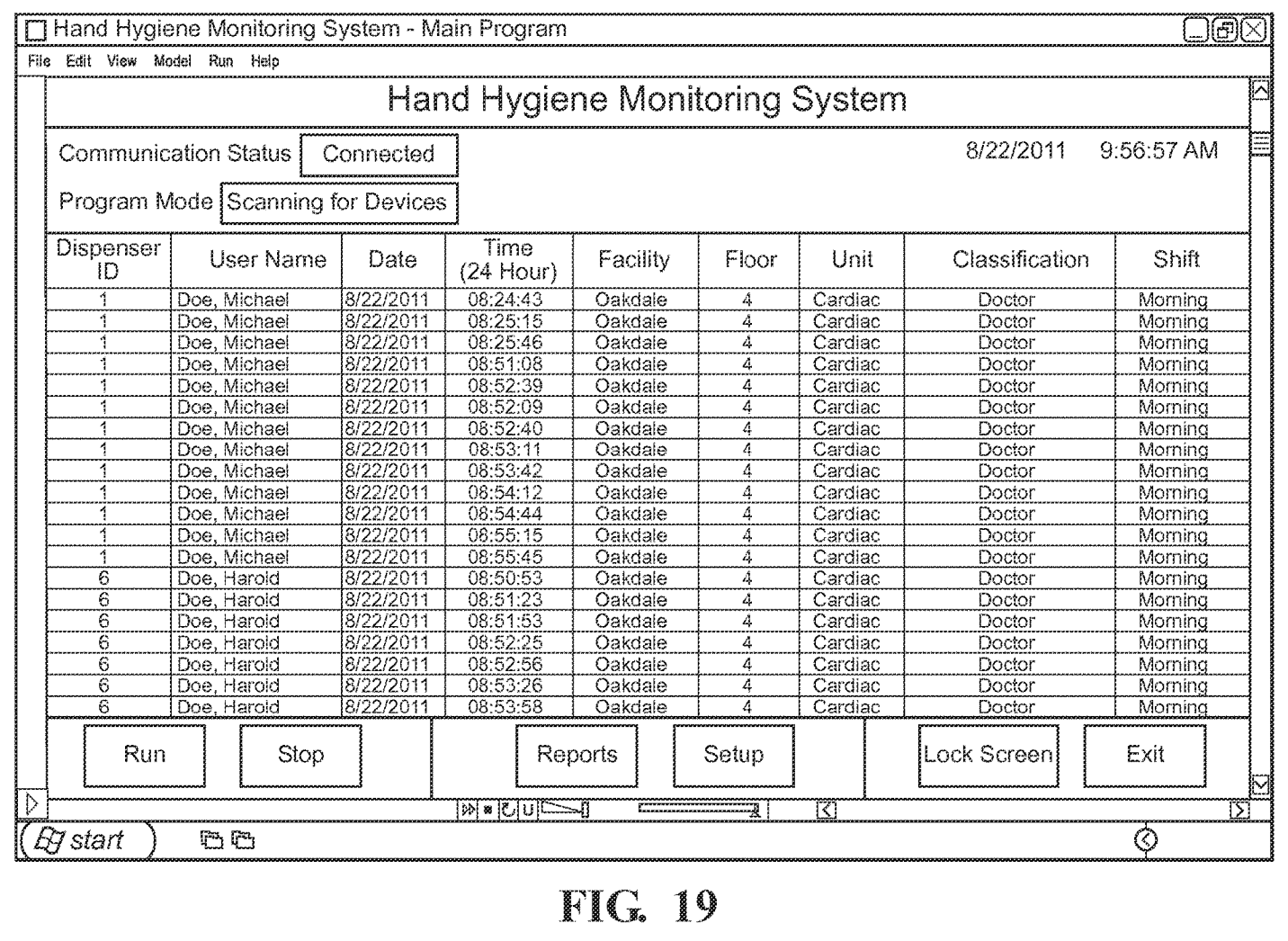

FIG. 19 shows a screen shot of the main monitoring interface. As shown, the main monitoring interface indicates the "Communication Status" of the software 302, i.e., the status indication of whether the software is currently receiving data. The software also tracks the preferred "Program Mode" of communication for the monitoring system 30. The modes of communication include continuously scanning for dispenser assemblies, or alternatively, only scanning for devices when prompted. As shown, the monitoring system 300 is currently in a scanning mode. The software 302 displays fields of the data such as "Dispenser ID," "User Name," "Date," "Time," "Facility," "Floor," "Unit," "Classification," and "Shift." Another field for the data, which is not shown, may include an "Alert—No Dispense" field. If this field is marked, then the user was alerted to dispense disinfectant, but failed to comply. The data is either stored first in the database and then displayed on the main monitoring interface, or the data is displayed first and then stored in the database. On this screen of the software 302, the user can select toggle buttons labeled "Reports" or "Setup." If "Reports" is selected, then the user is given many options of how to present the monitored data in a useful report format. If "Setup" is selected, then the user can set certain preferences.

Figure 20:
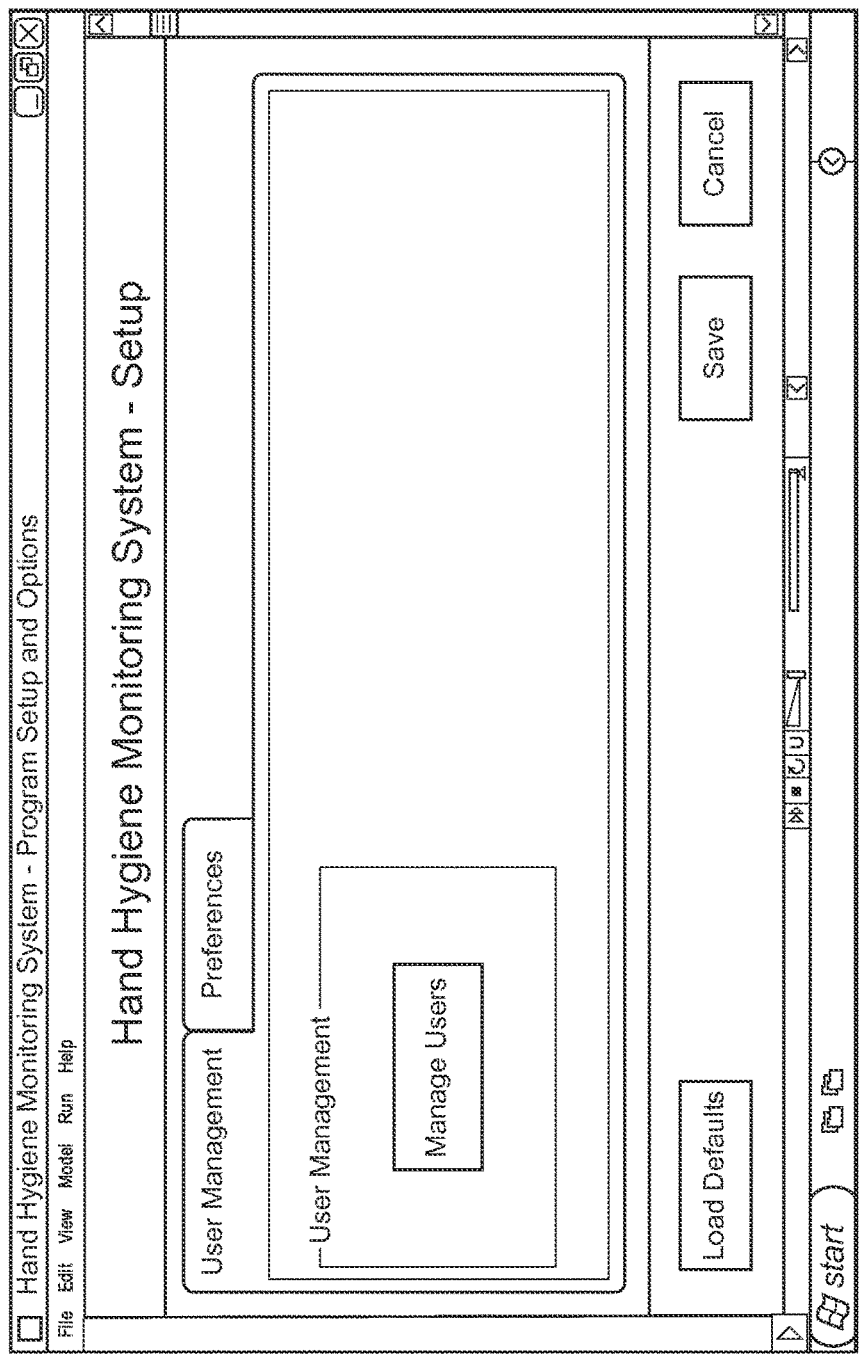
Figure 22:
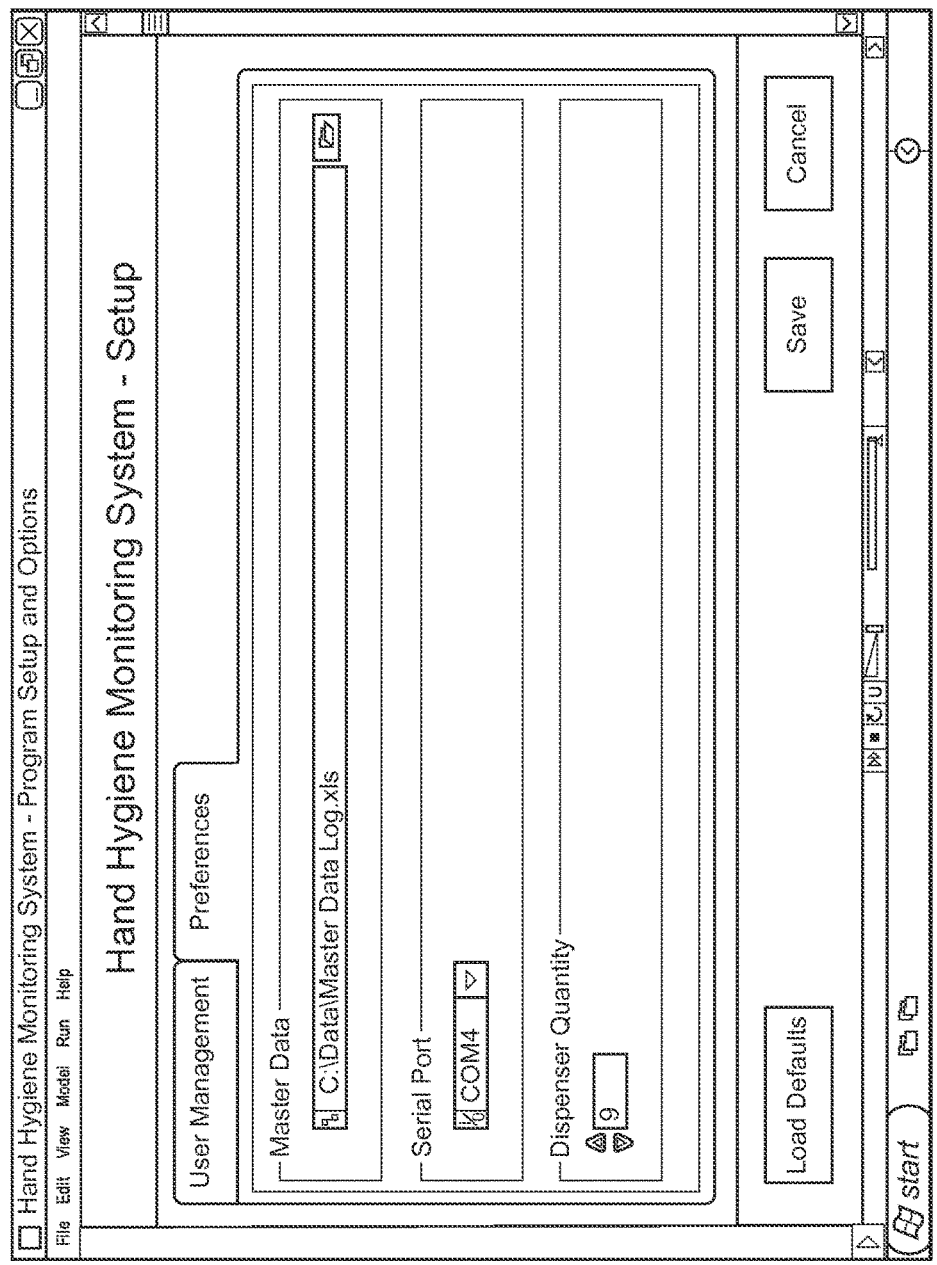

FIG. 20 illustrates a screen shot of the "Setup" feature of the software 302. In a first tab labeled "User Management," there is a toggle button for the user to select labeled "Manage Users." FIG. 21 shows the screen presented by the software after selecting the toggle button "Manage Users." In FIG. 21, new users are entered into the monitoring system 300 for tracking. They are assigned a dispenser assembly 10 and the "Dispenser ID" for each dispenser assembly 10 is correlated to the "User Name," "Facility," "Floor," "Unit," "Classification," and "Shift" of the user by entering that information into the form shown in FIG. 21. FIG. 22 illustrates a "Preferences" tab that can be used to change the location to which the data is stored. As shown, the data is stored in a master log that is a Microsoft Excel spreadsheet. In this case, the Microsoft Excel spreadsheet is the database in which the data is stored.

In some embodiments, electronic records could be kept for a medical practitioner based on his/her appointments via a custom software application and monitoring system. As a result, data could be provided which compares dispensing events to the electronic files and appointments to determine the frequency and adequacy of use of the dispenser assembly 10. The data could likewise be integrated into their electronic medical record and appointment system. This data could be used to determine the efficiency of the medical practitioner by comparing appointment time versus actual time patient was seen.

In yet other alternative embodiments, a pager and/or mobile phone may be integrated with the dispenser assembly 10 to make carrying the dispenser assembly 10 more convenient for the users. In these embodiments, the dispenser assembly 10 is equipped with a separate transmitter, receiver, and other equipment necessary for a pager and/or mobile phone as is well known in the art. In other embodiments, the same transceiver 82 could be used to carry out the functions of the pager and/or mobile phone.

In further embodiments, the dispenser assembly has a sensor that detects the presence of infectious pathogens and sets off an alarm upon detection of the pathogen prompting use and/or evacuation. Further, it is known that many airborne pathogens are most widely transmitted and present immediately after a cough or a sneeze. An additional feature of these versions is a microphone or pressure sensor that detects nearby coughs and sneezes by the sounds and/or change in atmospheric pressure thereby setting off the alarm to dispense disinfectant fluid and/or evacuate from the immediate premises.

Obviously many modifications and variations of the present invention are possible in light of the above description. While this description is directed to particular embodiments, it is understood that those skilled in the art may conceive of modifications and/or variations to the specific embodiments shown and described herein. For instance, references to a transmitter or receiver are not meant to be limiting in any way and may simply be the transmitting or receiving portions of a transceiver or other communication component. Also, references to transceivers can be understood in certain embodiments to refer to separate transmitters/receivers that separately transmit and receive, respectively, signals or data and can also refer to devices that communicate using different standards such as Zigbee or Bluetooth standards. Similarly, references to wired or wireless connections are not meant to be limiting in any way to particular modes of electronic communication. For instance, communication may employ any of a variety of communication protocols or standards. Any modifications or variations, which fall within the purview of this description, are intended to be included herein as well. It is understood that the description herein is intended to be illustrative only and is not intended to be limited.

What is claimed is:

1. A system for monitoring hand hygiene, said system comprising:
a handheld electronic device configured to generate device location data and to be carried by a user;
a portable dispenser assembly for being worn by the user to dispense disinfectant fluid from a container in a plurality of dispensing events, said assembly being separate from said handheld electronic device and including:
a main housing defining a cavity for receiving the container in an inverted position and defining an opening into said cavity through which the container is inserted in the inverted position so that a stem is directed downwardly in said main housing;
said main housing including a bottom wall, a side wall, a nozzle fixed with respect to said walls wherein said nozzle defines an inlet opposite said opening for receiving the stem of the container in the inverted position and said nozzle defines an outlet configured to direct the disinfectant fluid from the container laterally toward the user when the user depresses the container relative to said main housing to dispense the disinfectant fluid from the container; and
a mounting element coupled to said main housing and configured to attach said assembly to the user so that the container is capable of being oriented in the inverted position with respect to the user; and
an electronics unit coupled to said main housing to generate event data relating to the dispensing events;
a monitoring system to receive the device location data and the event data relating to the dispensing events for evaluating hand hygiene of the user.

2. The system as set forth in claim 1 wherein said handheld electronic device includes a radio frequency receiver and said electronics unit includes a radio frequency transmitter for communicating the event data from said electronics unit to said handheld electronic device.

3. The system as set forth in claim 1 wherein said handheld electronic device includes a radio frequency transmitter and said electronics unit includes a radio frequency receiver for communicating the device location data from said handheld electronic device to said electronics unit.

4. The system as set forth in claim 1 including an electronic emitter for generating an activation signal to prompt a dispensing event wherein said electronics unit includes a controller and a sensor operatively connected to said controller for detecting the activation signal from said electronic emitter.

5. The system as set forth in claim 4 wherein:
said electronics unit includes a first alarm generator in communication with said controller, said first alarm generator including at least one of a first visual annunciator, a first audible annunciator, or a first tactile annunciator; and
said controller is configured to activate said first alarm generator to generate a first alarm after said sensor receives the activation signal from said electronic emitter, and said controller is configured to terminate the first alarm generated by said first alarm generator in response to detecting a dispensing event.

6. The system as set forth in claim 5 wherein said electronics unit includes a second alarm generator including at least one of a second visual annunciator, a second audible annunciator, or a second tactile annunciator, wherein said controller is configured to activate said second alarm generator to generate a second alarm after said sensor receives the activation signal from said electronic emitter and after activation of said first alarm generator.

7. The system as set forth in claim 6 wherein said controller is configured to provide a delay of a predetermined period of time before activating said first alarm generator to generate the first alarm after detection of the activation signal.

8. The system as set forth in claim 7 wherein said sensor includes one of a wireless sensor, a radio frequency identification tag, a radio frequency identification reader, an infrared sensor, a radio frequency antenna, or an ultrasound sensor.

9. The system as set forth in claim 8 wherein said electronic emitter includes a wire antenna configured for mounting to a bed.

10. The system as set forth in claim 4 wherein said controller includes a counter to count dispensing events, said controller configured to alert the user of low disinfectant fluid and automatically reset said counter upon replacement of the container.

11. The system as set forth in claim 4 wherein said electronic emitter includes a motion detector having an infrared sensor for detecting the user and a radio frequency transmitter operatively connected to said motion detector to generate the activation signal in response to detecting the user.

12. The system as set forth in claim 11 wherein said motion detector is configured to generate a plurality of infrared beams so that said controller is able to determine a direction of motion of the user.

13. The system as set forth in claim 1 wherein said assembly includes a flexible portion protruding into said cavity for being engaged by the container and flex when the container is inserted into said cavity.

14. The system as set forth in claim 4 wherein said electronic emitter is configured to focus and pulse the activation signal for receipt by said sensor of said electronics unit to prevent inadvertent activation of other portable dispenser assemblies.

15. The system as set forth in claim 4 wherein said electronic emitter includes a reader configured to read identification tags, said electronic emitter configured to generate the activation signal in response to reading an identification tag of the user if the identification tag of the user is a specified identification tag configured to cause said electronic emitter to generate the activation signal.

16. The system as set forth in claim 6 wherein said controller is configured to distinguish between a plurality of different activation signals associated with a plurality of different user types and said controller is configured to generate the first alarm when the activation signal generated by said electronic emitter is associated with a user type assigned to said assembly.

17. The system as set forth in claim 1 wherein said assembly includes a second nozzle defining a second inlet for receiving a second disinfectant fluid from a second container and a second outlet for directing the second disinfectant fluid toward the user, said nozzles being spaced and fixed relative to each other.

18. A method for monitoring hand hygiene by a user, said method comprising the steps of:
providing a portable dispenser assembly for being worn by the user to dispense disinfectant fluid from a container in a plurality of dispensing events, the assembly including:
a main housing defining a cavity for receiving the container in an inverted position and defining an opening into said cavity through which the container is inserted in the inverted position so that a stem is directed downwardly in said main housing;
said main housing including a bottom wall, a side wall, a nozzle fixed with respect to said walls wherein said nozzle defines an inlet opposite said opening for receiving the stem of the container in the inverted position and said nozzle defines an outlet configured to direct the disinfectant fluid from the container laterally toward the user when the user depresses the container relative to said main housing to dispense the disinfectant fluid from the container;
a mounting element coupled to said main housing and configured to attach said assembly to the user so that the container is capable of being oriented in the inverted position with respect to the user; and
an electronics unit coupled to the main housing to generate event data relating to the dispensing events; and
collecting, at a monitoring system, the event data generated by the electronics unit; and
collecting, at the monitoring system, device location data generated by a handheld electronic device, wherein the handheld electronic device is separate from the portable dispenser assembly and configured to be carried by a user and communicate with the electronics unit.

19. The system as set forth in claim 1 wherein
said electronics unit includes a controller, a sensor configured to receive an activation signal, and an alarm generator including at least one of a visual annunciator, an audible annunciator, or a tactile annunciator; and
said controller is configured to activate said alarm generator to generate an alarm after said sensor receives the activation signal and to terminate the alarm generated by said alarm generator in response to detecting a dispensing event.

20. A system for monitoring hand hygiene, said system comprising:
an electronic emitter for generating an activation signal to prompt a dispensing event;
a handheld electronic device configured to generate device location data and to be carried by a user;
a portable dispenser assembly for being worn by the user to dispense disinfectant fluid from a container in a plurality of dispensing events, said assembly being separate from said handheld electronic device and including:
a main housing defining a cavity for receiving the container;
a nozzle defining an inlet for receiving the disinfectant fluid from the container and an outlet for directing the disinfectant fluid toward the user; and
an electronics unit including:
a controller and a sensor operatively connected to said controller for detecting the activation signal from said electronic emitter;
a first alarm generator in communication with said controller, said first alarm generator including at least one of a first visual annunciator, a first audible annunciator, or a first tactile annunciator wherein said controller is configured to activate said first alarm generator to generate a first alarm after said sensor receives the activation signal from said electronic emitter, and said controller is configured to terminate the first alarm generated by said first alarm generator in response to detecting a dispensing event;
a second alarm generator including at least one of a second visual annunciator, a second audible annunciator, or a second tactile annunciator, wherein said controller is configured to activate said second alarm generator to generate a second alarm after said sensor receives the activation signal from said electronic emitter and after activation of said first alarm generator;
wherein said controller is configured to distinguish between a plurality of different activation signals associated with a plurality of different user types and said controller is configured to generate the first alarm when the activation signal generated by said electronic emitter is associated with a user type assigned to said assembly; and
a monitoring system to receive the device location data and event data relating to the dispensing events for evaluating hand hygiene of the user.

* * * * *